(12) United States Patent
Gonsalves

(10) Patent No.: US 10,052,434 B2
(45) Date of Patent: Aug. 21, 2018

(54) DEVICES AND METHODS FOR MINIMIZING INFUSION OF AIR INTO AN INTRAVENOUS FLUID LINE FROM AN INTRAVENOUS FLUID BAG BY A PRESSURE INFUSION CUFF

(71) Applicant: University of Florida Research Foundation, Inc., Gainesville, FL (US)

(72) Inventor: Drew B. Gonsalves, Jacksonville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 0 days.

(21) Appl. No.: 15/520,234

(22) PCT Filed: Nov. 10, 2015

(86) PCT No.: PCT/US2015/059887
§ 371 (c)(1),
(2) Date: Apr. 19, 2017

(87) PCT Pub. No.: WO2016/089554
PCT Pub. Date: Jun. 9, 2016

(65) Prior Publication Data
US 2017/0333628 A1 Nov. 23, 2017

Related U.S. Application Data

(60) Provisional application No. 62/190,388, filed on Jul. 9, 2015, provisional application No. 62/087,411, filed on Dec. 4, 2014.

(51) Int. Cl.
*A61M 5/168* (2006.01)
*A61M 5/152* (2006.01)
(Continued)

(52) U.S. Cl.
CPC ........... *A61M 5/16822* (2013.01); *A61J 1/10* (2013.01); *A61M 5/1417* (2013.01);
(Continued)

(58) Field of Classification Search
CPC .. A61M 5/148; A61M 5/1483; A61M 5/1486; A61M 2005/14513; A45D 8/20; A45D 8/24; B65D 33/1675
See application file for complete search history.

(56) References Cited

U.S. PATENT DOCUMENTS

| 4,090,514 A | 5/1978 | Hinck et al. |
| 4,657,160 A | 4/1987 | Woods et al. |

(Continued)

FOREIGN PATENT DOCUMENTS

| JP | 11-123241 | 5/1999 |
| KR | 20-0404013 | 12/2005 |

OTHER PUBLICATIONS

Ostrup, R.C. et al., "Continuous monitoring of intracranial pressure with a miniaturized fiber optic device," *Journal of Neurosurgery*, Aug. 1987, pp. 206-209, vol. 67, No. 2.

*Primary Examiner* — Nathan R Price
*Assistant Examiner* — Justin L Zamory
(74) *Attorney, Agent, or Firm* — Saliwanchik, Lloyd & Eisenschenk

(57) ABSTRACT

The problem of infusing air into IV tubing and into a patient from a IV fluid bag inside a pressure infusion cuff is solved by collar embodiments that inhibit the air from being forced into the IV tubing. A collar can include one or more curved arms that create a channel in which that part of the fluid bag is protected against being squeezed by a pressure infusion cuff. A collar allows the fluid bag to be squeezed by the pressure infusion cuff until such time that the fluid level is sufficiently reduced that the collar can inhibit further pres- (Continued)

sure on the fluid bag by the pressure infusion cuff. Also disclosed is a fluid bag and a pressure infusion cuff that are modified to have a collar incorporated therewith.

8 Claims, 24 Drawing Sheets

(51) Int. Cl.
*A61M 5/14* (2006.01)
*A61M 5/36* (2006.01)
*A61J 1/10* (2006.01)
*A61M 5/148* (2006.01)

(52) U.S. Cl.
CPC .......... *A61M 5/1483* (2013.01); *A61M 5/152* (2013.01); *A61M 5/36* (2013.01)

(56) References Cited

U.S. PATENT DOCUMENTS

| | | | |
|---|---|---|---|
| 4,735,613 A | | 4/1988 | Bellin et al. |
| 4,872,483 A | | 10/1989 | Shah |
| 5,147,310 A | * | 9/1992 | Giannini ............. A61M 5/1483 128/DIG. 12 |
| 5,211,201 A | | 5/1993 | Kamen et al. |
| 5,465,742 A | * | 11/1995 | Dudley .................... A45D 8/24 132/212 |
| 6,406,458 B1 | * | 6/2002 | Tillander ............. A61M 5/1483 604/147 |
| 2004/0154633 A1 | * | 8/2004 | Rogers ..................... A45D 8/20 132/277 |
| 2009/0126825 A1 | * | 5/2009 | Eliuk ...................... B65B 3/003 141/1 |
| 2010/0324532 A1 | | 12/2010 | Marak et al. |
| 2011/0118666 A1 | | 5/2011 | Sivilich et al. |

* cited by examiner

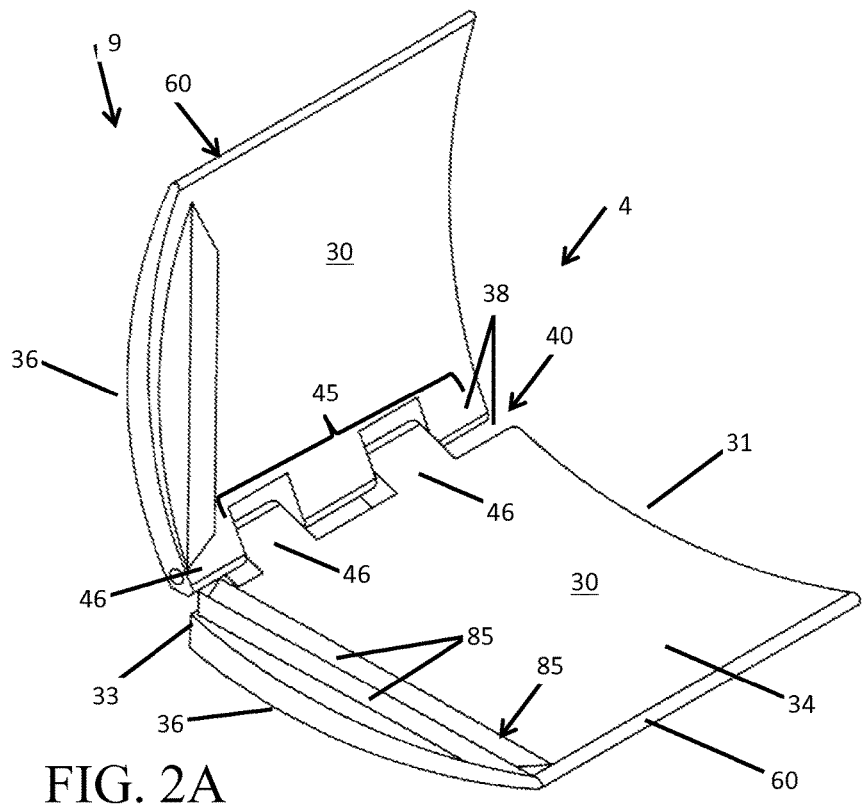
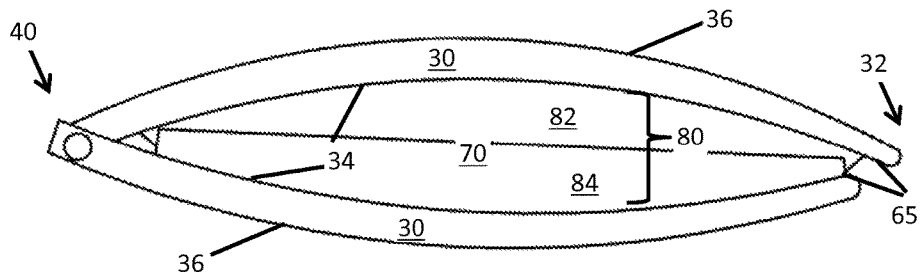
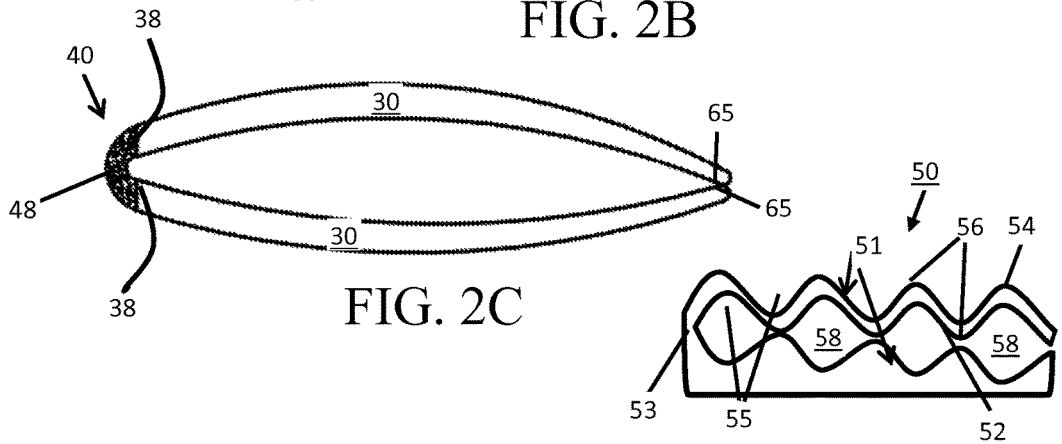

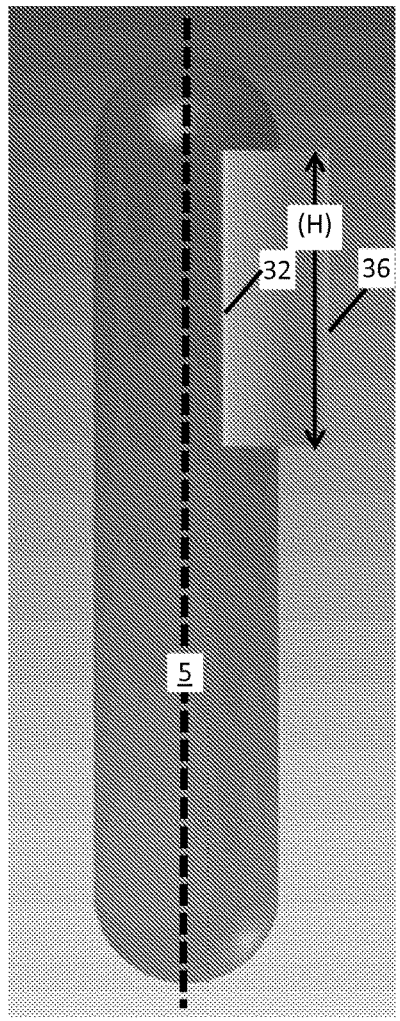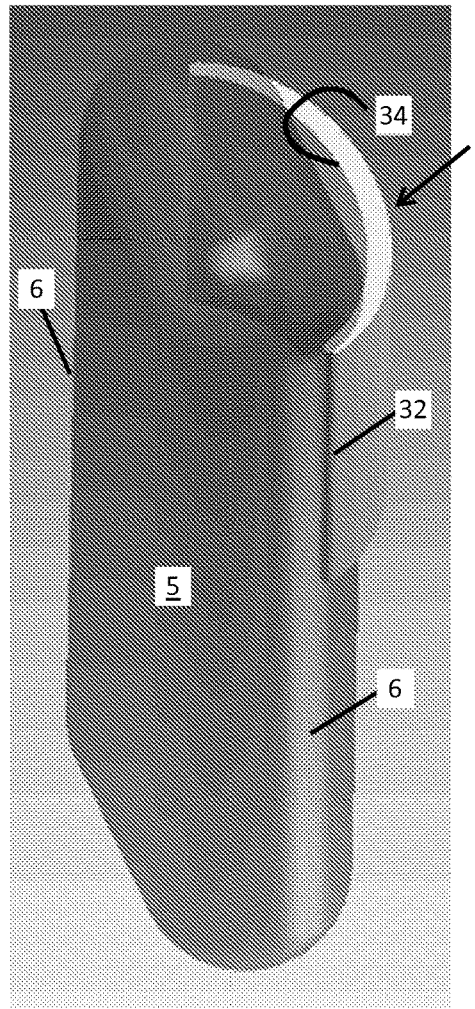
FIG. 9A   FIG. 9B
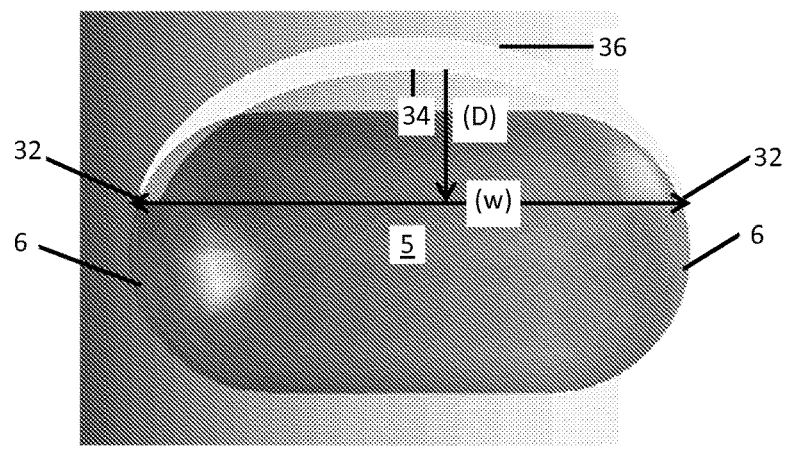
FIG. 9C

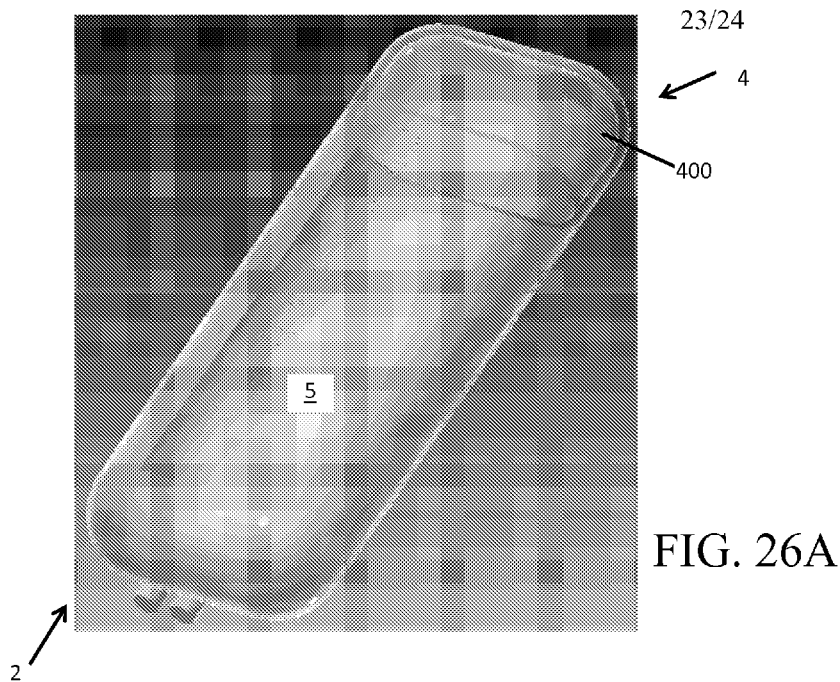
FIG. 26A
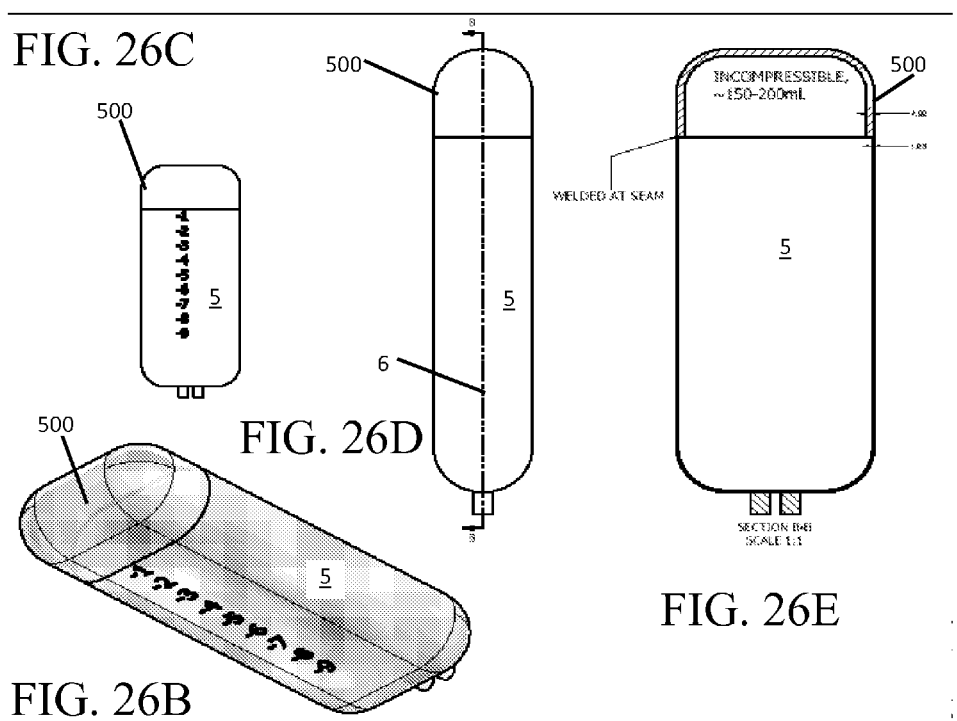
FIG. 26C
FIG. 26D
FIG. 26E
FIG. 26B

DEVICES AND METHODS FOR MINIMIZING INFUSION OF AIR INTO AN INTRAVENOUS FLUID LINE FROM AN INTRAVENOUS FLUID BAG BY A PRESSURE INFUSION CUFF

CROSS-REFERENCE TO RELATED APPLICATIONS

This application is the U.S. national stage application of International patent application No. PCT/US2015/059887, filed Nov. 10, 2015, which claims the benefit of U.S. Provisional Application Ser. No. 62/190,388, filed Jul. 9, 2015, and U.S. Provisional Application Ser. No. 62/087,411, filed Dec. 4, 2014, the disclosures of which are hereby incorporated by reference in their entireties, including all figures, tables and drawings.

BACKGROUND OF INVENTION

When a patient is in need of intravenous fluids, an intravenous (IV) fluid apparatus, including IV tubing and IV catheter connected to a bag of fluid, is used to infuse fluid directly into a vessel. The fluid bag is typically elevated above the patient so that gravity can aid in moving the fluid through a drip chamber and into the line and catheter. The size or diameter of the intravenous tubing and catheter can impact how quickly fluid is delivered into the vessels of the patient.

To increase or control the rate of fluid delivery, a pressure infusion cuff can be placed around the fluid bag. A pressure infusion cuff is a general term for inflatable devices that are in the form of a sleeve for receiving a fluid bag or that opens up or lays flat and can be wrapped around the fluid bag. The pressure infusion cuff can be inflated through use of an inflation bulb. The inflated pressure infusion cuff squeezes or compresses the fluid bag so as to increase the rate at which the fluid drips out of the bag.

BRIEF SUMMARY

Collars for use with pressure infusion cuffs are provided. In general, a collar is a device that can control the compression applied to a portion of a fluid bag by inhibiting the pressure infusion cuff from compressing or from fully compressing the volume of the fluid bag encompassed or contained by the collar. More particularly, when a collar embodiment of the subject invention is emplaced on or around a fluid bag, a pressure infusion cuff is inhibited from compressing or fully compressing that area of the fluid bag.

According to one implementation, a collar includes two arms that are hingeably joined at one end so that in a "closed" position, a pocket, void space, or channel is formed with a volume between the arms that can inhibit compression or at least complete evacuation of that portion of a fluid bag contained within that volume. In another implementation, a collar includes a single arm that can form during use or can have a preformed channel also with a volume that can inhibit compression of that portion of a fluid bag contained within that formed or pre-formed volume. In yet another implementation there is provided a tubular collar that surrounds a portion of a fluid bag, where that portion of the fluid bag within the channel of the tubular collar is inhibited from being compressed or squeezed. In still another implementation, the collar has a cup-like shape with one or more access ports for attachment of tubes and other accessories through the collar to the fluid bag. Ideally, the volume of the channel provided by the collar at its limiting position creates a trap or pocket for any air that may remain in an IV fluid bag. At the least, a collar of the subject invention will inhibit a portion of a fluid bag from being completely compressed and thereby further inhibiting any air in the fluid bag from being forcibly expressed from the fluid bag. In some implementations, one or more sealing edges can be included on the collar. The one or more sealing edges can act to further isolate the air pocket within the bag to be within the channel formed by the one or more arms of the collar.

Alternative embodiments can incorporate a collar of the subject invention with a fluid bag or a pressure infusion cuff. These could be more convenient options, particularly in situations where the ability to manipulate a collar, fluid bag, and pressure infusion cuff is not feasible. One implementation of a fluid bag has a collar incorporated into or on the structure of the fluid bag, such that the fluid bag and collar are inseparable. Another implementation is a pressure infusion cuff with a collar of the subject invention incorporated with the structure of the pressure infusion cuff, such that they, too, are inseparable. An alternative implementation of a pressure infusion cuff has a pocket or attachment mechanism by which a collar can be secured to and maintained on the pressure infusion cuff until removed.

The dimensions and curvature of the one or more collar embodiments can be configured so that by the time the collar operates to isolate any air bubble or air pocket therein, the pressure infusion cuff has been sufficiently effective in evacuating most of the fluid from the fluid bag. The described collars inhibit the accidental infusion or injection of air into the vein of a patient from an IV fluid bag in an upright position with fluid exit towards ground, controlled by a pressure infusion cuff, while not adversely interfering with the ability of a pressure infusion cuff to squeeze the fluid bag.

In use, certain implementations of the described collars can be positioned around the outside of an IV fluid bag. The IV fluid bag can be vertically positioned, such that fluid exits from the bottom end of the fluid bag, with any air in the bag remaining above the fluid. The shapes and rigidity of the collars create a channel in which the IV fluid bag can be disposed and which can prevent the pressure infusion cuff from fully compressing the IV fluid bag, thereby inhibiting any air in the bag within the space generated by the volume within the arm or arms of the collars from being pressurized. After the fluid bag is emptied or is no longer required, the collar can be removed and either used again, disposed of, or recycled.

It should be noted that this Brief Summary is provided to generally introduce the reader in a simplified form to one or more select concepts described below in the Detailed Disclosure. This Summary is not intended to identify key and/or required features of the claimed subject matter. Other aspects and further scope of applicability of the present invention will also become apparent from the detailed descriptions given herein. It should be understood, however, that the detailed descriptions, while indicating preferred embodiments of the invention, are given by way of illustration only, since various changes and modifications within the spirit and scope of the invention will become apparent from such descriptions. The invention is defined by the claims below.

BRIEF DESCRIPTION OF DRAWINGS

In order that a more precise understanding of the above recited invention can be obtained, a more particular description of the invention briefly described above will be rendered by reference to specific embodiments thereof that are illustrated in the appended drawings. The drawings presented herein may not be drawn to scale and any reference to dimensions in the drawings or the following description is specific to the embodiments disclosed. Any variations of these dimensions that will allow the subject invention to function for its intended purpose are considered to be within the scope of the subject invention. Thus, understanding that these drawings depict only typical embodiments of the invention and are not therefore to be considered as limiting in scope, the invention will be described and explained with additional specificity and detail through the use of the accompanying drawings in which:

FIG. 2A is a perspective view of an embodiment of a collar, according to the subject invention. This embodiment includes sealing edges on the arms.

FIG. 2B is a proximal end elevation view of an embodiment of a collar, according to the subject invention. This view illustrates how one embodiment of seal components can fit together.

FIG. 2C is a proximal end elevation view of an alternative embodiment of a collar that utilizes a flexure bearing.

FIG. 2D is a proximal end elevation view of another alternative embodiment of a collar having panels instead of arms, where there can be more than one concave area and more than one convex area on the internal side and/or the external side of each panel. Also illustrated is an example of a panel having a substantially flat surface with neither a convex area nor a concave area.

FIG. 9A is a side elevation view of a representative IV fluid bag showing an embodiment of a single-arm collar placed thereon.

FIG. 9B is a rear perspective view of a representative IV fluid bag showing an embodiment of a single-arm collar placed thereon.

FIG. 9C is a proximal end elevation view of a representative IV fluid bag showing an embodiment of a single-arm collar placed thereon.

FIG. 21A is a perspective view of an embodiment of a cap collar with the arms rotated to an open position; FIG. 21B is a perspective view showing the convex surface with a slit for hanging the cap collar and/or a fluid bag and pressure infusion cuff; and FIG. 21C shows a cap collar emplaced on a fluid bag placed on a pressure infusion cuff that has not been closed.

FIG. 22A is a perspective view showing the entry way; FIG. 22B shows the collar around the distal end of a fluid bag placed on a pressure infusion cuff that has not been closed; and FIG. 22C shows the rigid collar with wings around about the proximal end of a fluid bag placed on a pressure infusion cuff that has not been closed.

FIG. 23A is a perspective view and FIG. 23B shows the rigid collar with attached wings on a fluid bag.

FIG. 24A shows a flex collar in an open or uncurved configuration. FIG. 24B shows a flex collar against a pressure infusion cuff to illustrate how closing the pressure infusion cuff will cause the side edges to curve around and over a fluid bag placed therein.

FIGS. 25A, 25B and 25C show an embodiment of a shelf collar wherein FIG. 25A is a perspective view showing the interior of the channel, FIG. 25B is a perspective view showing the port through the shelf and FIG. 25C shows the shelf collar with a fluid bag therein and against an open pressure infusion cuff, prior to being secured around the shelf collar and the fluid bag.

FIGS. 26A, 26B, 26C, 26D, and 26E show an embodiment of a collared fluid bag. In the embodiment shown, a fluid bag is modified with a cap collar, where FIG. 26A is a perspective view of a collared fluid bag; FIG. 26B is another perspective view; FIG. 26C is a front elevation view; FIG. 26D is a side elevation view; and FIG. 26E is a front elevation cross-sectional view showing how a capped collar can be incorporated into the fluid bag.

DETAILED DISCLOSURE

Figure 1A:
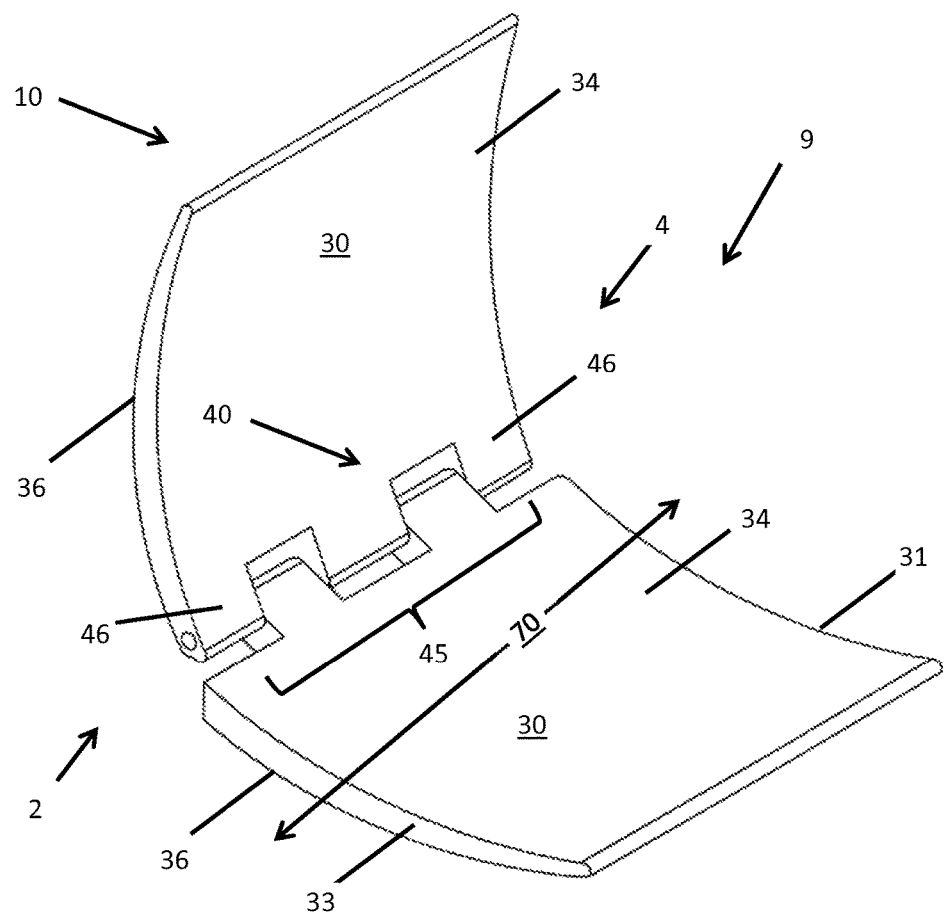
FIG. 1A is a perspective view of an embodiment of a collar, according to the subject invention.

Collars for use with pressure infusion cuffs are provided. IV fluid bags commonly contain a discrete amount of air, which can aid in observing the fluid meniscus. Typically, the air is evacuated from the IV fluid bag prior to use. However, during an emergency situation, there may not be time to evacuate the air or partially emptied IV bags are reused and contain much higher amounts of air. In a gravity-fed IV arrangement, a percentage of the air in the bag will remain in the bag, even after the fluid is completely drained out. However, when a pressure infusion cuff is utilized it is possible for the air remaining in the fluid bag to be forced into the tubing after the bag is emptied of fluid and into the patient. If the air is infused into the patient, it can cause a fatal air embolus. Thus, the use of a pressure infusion cuff on an IV bag can increase the risk of the air in the IV bag being infused into the vessels of the patient.

When an IV fluid bag is evacuated or emptied into the IV tubing by the force of gravity, air can enter the tubing when the fluid is completely evacuated, but the air does not reach the patient. The typical central venous pressure of the human body is a positive value of about 0-10 mmHg. This creates some amount of back pressure that an infusion system would have to overcome in order to bolus air into a patient.

However, when using a pressure infusion cuff on a fluid bag, the air may be forced into the tubing and into the patient due to pressures exceeding the central venous pressure of the patient. Typical infusion cuff pressures are about 300 mmHg. Advantageously, the described collars are a relatively inexpensive and highly effective solution to reduce the ability of a pressure infusion cuff to squeeze a fluid bag to the point where the air is forced into the tubing and into the patient. Indeed, by selection of an appropriate collar with minimum enclosed volume for a particular sized IV fluid bag, the described collars can prevent an accidental air embolism through an IV infusion without the need for electronic sensors or other secondary devices for monitoring an IV fluid bag.

The following description will disclose that certain embodiments of the subject invention are particularly useful in the field of medical intravenous fluid procedures, in particular with devices such as IV pressure infusion cuffs that can be used to increase the drip rate or rate of evacuation of fluid from an IV fluid bag. However, a person with skill in the art will be able to recognize numerous other uses that would be applicable to the devices and methods of the subject invention. While the subject application describes, and many of the terms herein relate to, a use for intravenous infusion of fluids to a patient, other modifications apparent to a person with skill in the art and having benefit of the subject disclosure are contemplated to be within the scope of the present invention.

In the description that follows, a number of terms used are related to intravenous administration of infusion of fluids to a patient. In order to provide a clear and consistent understanding of the specification and claims, including the scope to be given such terms, the following definitions are provided.

The term "patient" as used herein refers to any vertebrate or invertebrate species on which fluid infusion can be performed, including neonates to the elderly and all ages in between in any species. Vertebrate species, in particular those with a closed circulatory system such as humans and other mammals, are specifically suited for treatment with the embodiments of the subject invention. Mammalian species that can benefit from the disclosed devices and methods of treatment include, and are not limited to, apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bears, lions, tigers, panthers, elephants, hippopotamuses, rhinoceroses, giraffes, antelopes, sloths, gazelles, zebras, wildebeests, prairie dogs, koala bears, kangaroos, opossums, raccoons, pandas, hyenas, seals, sea lions, elephant seals, otters, porpoises, dolphins, and whales.

The terms "IV fluid bag," "fluid bag," and "bag" are used interchangeably herein to refer to any type of flexible container apparatus used to infuse fluids into a patient. More specifically, it refers to flexible container apparatuses that operate under the force of gravity to infuse fluids into a patient.

Also, as used herein, and unless otherwise specifically stated, the terms "operable communication," "operable connection," "operably connected," "cooperatively engaged" and grammatical variations thereof mean that the particular elements are connected in such a way that they cooperate to achieve their intended function or functions. The "connection" or "engagement" may be direct or indirect.

Finally, reference is made throughout the application to the "proximal end" and "distal end." As used herein, the proximal end is that end of a collar device of the subject invention or that end of an IV fluid bag that is placed closest to a patient. More specifically, the proximal end is that end of an IV fluid bag from which fluid flows out and that end of a collar device which is placed closest to the fluid outflow opening. Conversely, the distal end is that end of a collar or IV fluid bag that is located furthest from a patient. More specifically the distal end is that end of an IV fluid bag typically connected to an IV pole and, with regard to a collar device, is that end that would be placed closest to the end of an IV fluid bag that is attached to an IV pole, or that end placed furthest from the outflow opening.

The present invention is more particularly described in the following examples that are intended to be illustrative only since numerous modifications and variations therein will be apparent to those skilled in the art. As used in the specification and in the claims, the singular for "a," "an" and "the" include plural referents unless the context clearly dictates otherwise.

Reference will be made to the attached FIGS. 1-27, on which, where applicable, the same reference numerals are used throughout to indicate the same or similar components or features, if they are the same on the different collar 9 embodiments described herein.

FIGS. 1-8D illustrate different embodiments of clip collars 10 that have two or more arms, where each arm 30 has a proximal end 2 and a distal end 4, and at least one side edge 32, a concave surface 34 that can form a channel 70 when the arms are close together, and an opposing convex surface 36 against which a pressure infusion cuff 8 can make contact, instead of making contact with the fluid bag. Further, the clip collar embodiments described herein can have one of the side edges of an arm modified as hinged edges 38 that are joined to form an articulating side 40, where the two or more hinged edges on the arms are operably and rotatably attached, and can have at least one other side edge modified to be a closing side 60 where the at least two arms can come together on facing edges 65 that are generally opposite to the articulating side. The arms can be curved or have a concave surface 34, where the curvature is between the hinged edge 38 that forms the articulating side 40 and the side edge 32 that forms the closing side 60. This can form a channel 70, which can be opened or closed depending upon the embodiment, between the articulating side and the side edge, where the direction 7 of the channel is generally parallel to the articulating side and/or the side edge.

Further, FIG. 9A through FIG. 20, illustrate embodiments of a rigid collar 100 having one arm 30, as similarly described above, where there is a proximal end 2 and a distal end 4, and at least two side edges 32, a concave surface 34 that can form a channel 70 with the interior wall of a pressure infusion cuff, and an opposing convex surface 36 against which a pressure infusion cuff 8 can make contact.

Figure 21A:
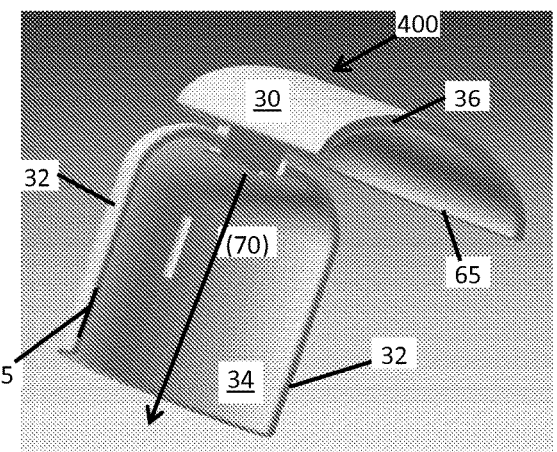
FIGS. 21A, 21B, and 21C illustrate embodiments of a cap collar, where
Figure 21B:
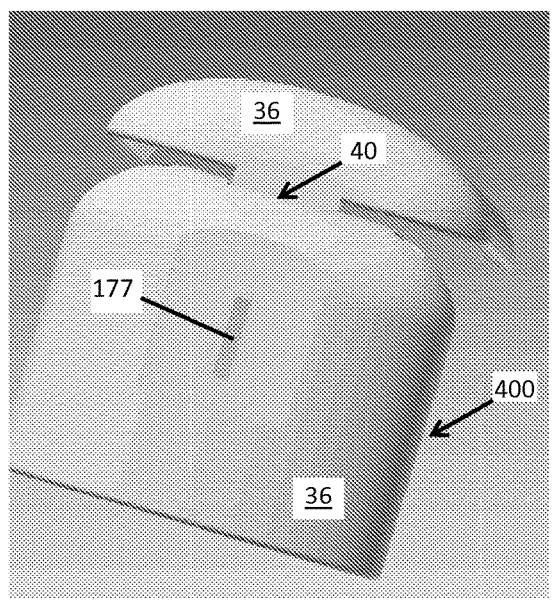
Figure 21C:
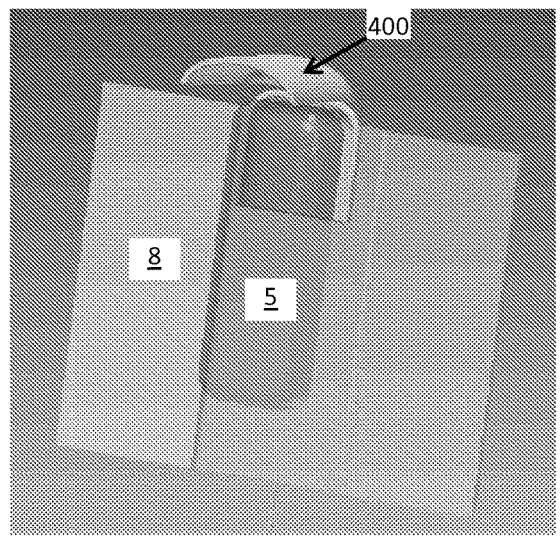

FIGS. 21A, 21B, and 21C illustrate an alternative of a clip collar embodiment. This embodiment includes two arms rotatably connected at an articulating side 40, but, the curvature is changed to be between the top edge 31 and the bottom edge 33, such that these two edges act as side edges 32, coming together to form two closing sides 60 that are perpendicular, or generally perpendicular, to the articulating side. The change in curvature of the arms, now being between the top and bottom edges, causes the channel direction to be generally perpendicular to the articulating side, so as to form a "cap" that can be placed over one end of a fluid bag.

Figure 7:
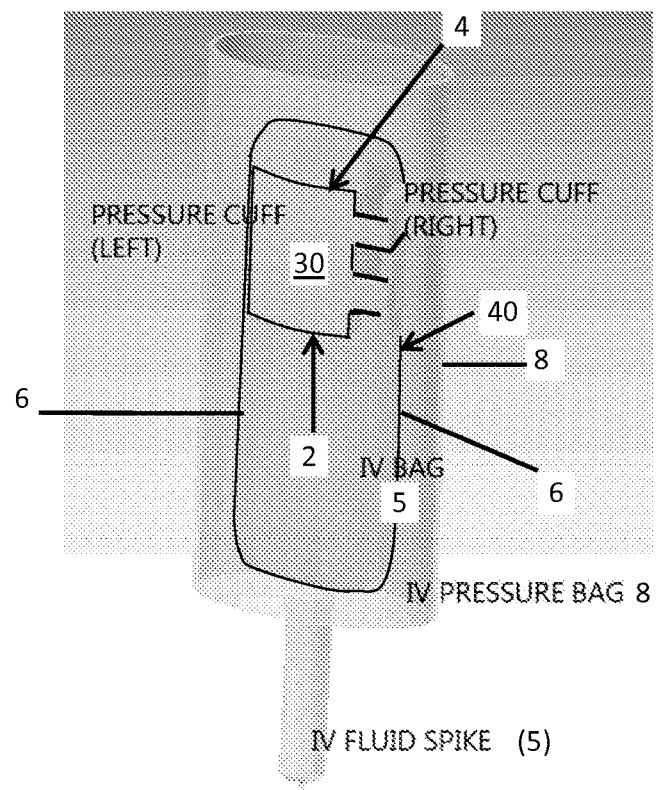
FIG. 7 is a perspective view of a collar embodiment of the subject invention positioned around an IV fluid bag, which has been placed inside a pressure infusion cuff.
Figure 8A:
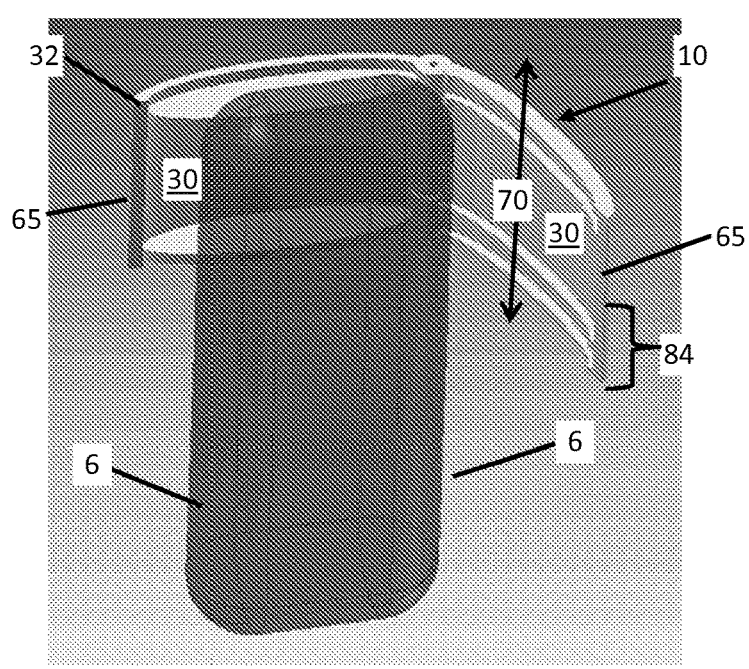
FIG. 8A is a perspective view of a representative IV fluid bag showing a collar embodiment of the subject invention being placed therearound.

With regard to an arm 30 utilized with either the rigid collar 100 or the clip collar 10 embodiments, the dimensions can vary depending upon the size of an IV fluid bag and any pressure infusion cuff 8 that it will be used with. A collar can extend from at or about one vertical side 6 to at or about the other vertical side of an IV fluid bag to capture or contain 100% of the air in the bag. However, it is not required that a collar extends fully from one vertical side to another or that 100% of the air in the bag be contained. As long as the dimensions of a collar allow it to capture or contain at least 30%, 35%, 40%, 45%, 50%, 55%, 60%, 65%, 70%, 75%, 80%, 85%, 90%, 95%, and/or 99%, and/or an amount in a range between any two of the listed values, any uncaptured air will also be inhibited from entering the IV tubing, due to the decreased pressure on the bag by the presence of the collar. Thus, it will be understood by the skilled artisan, that the width (W) and height (H) of the arms of the collar can vary considerably depending upon these and other factors. FIG. 7 shows one example of a collar that extends almost entirely across a fluid bag, from one vertical side 6 of the fluid bag to the other. FIG. 8A shows an embodiment where the collar extends completely across and beyond the side edges of a fluid bag. Variations in collar dimensions that provide the same functionality, in substantially the way as described herein, with substantially the same desired results, are within the scope of this invention.

As will be discussed in more detail below, the collar 9 embodiments of the subject invention can create at least one channel, cavity, or void in which an IV bag can be protected against full compression or evacuation by a pressure infusion cuff. To maintain the integrity of the channel when under pressure by a pressure infusion cuff, an arm can be a rigid or at least semi-rigid material that does not collapse or does not collapse fully when pressure is exerted against the convex surface. In addition, a collar can be made of a reusable material or a material that is disposable, such that a collar would only be used once or perhaps a few times before discard. It is within the skill of a person trained in the art, having benefit of the subject disclosure, to determine an appropriate material and dimensions for a collar 9 of the subject invention. Such variations are within the scope of the subject invention.

In a particular embodiment, the maximum thickness (T), between the concave surface 34 and the convex surface 36, of the material utilized for a collar is between approximately 4 mm and approximately 7 mm. More specifically, the maximum thickness (T) of the material utilized for a collar is approximately 6 mm. However, the thickness of certain portions of a collar can be less than 4 mm, for example, in areas of a "living hinge" where the articulating side bends.

In the embodiments described herein, an arm 30 has at least one convex surface 36 and at least one opposing concave surface 34. The examples shown in FIGS. 1A-2B and 2A-2B, as well as FIGS. 10A-10D and 12A-12D illustrate both clip collars 10 and rigid collars 100 having arms with one concave surface and one convex surface. In these collar 9 embodiments, the convex surface 36 can be directed away from an IV fluid bag and presents a surface that a pressure infusion cuff can press against. The concave surface 34 can be directed towards and/or pressed against an IV fluid bag and presents a surface that an IV fluid bag can, at least initially, make contact with. The depth of the curvature of a concave surface can vary depending upon the embodiment, as will be discussed below. For example, with rigid collar embodiments, which have a single arm and can be positioned mostly on one side of a fluid bag, it can be advantageous for the depth of the concave surface to be greater than it would be for a clip collar 10 that utilizes two are more arms that go around either side of a fluid bag. However, this is not required for all embodiments and the depth of the concave surface could be the same as or similar for the different collar 9 embodiments disclosed herein.

The depth of the curvature on the concave surface of an arm can also depend upon the material utilized for an arm, the rigidity of the arm, the dimensions of the arm, and other factors that would be known to those with skill in the art. By way of example, a collar 9 of softer or more pliable materials that can at least partially collapse under pressure can require a concave surface that initially forms a channel 70 of greater volume than would a collar made of more rigid or less-pliable materials. This can allow the collar to be compressed and still retain an acceptable channel volume. Such variations in the volume of the channel and the curvature of a concave surface that provide the same function, in substantially the same way, with substantially the same result are within the scope of this invention.

A particular alternative embodiment of a collar 9 is a corrugated collar 50 having instead two panels 51 that are moveably and rotatably joined on an articulating edge 53, each panel having more than one concave area 55 and more than one convex area 56. With this embodiment, an internal surface 52 on each panel can be placed against an IV fluid bag and can have both concave areas 55 and convex areas 56, as illustrated, for example, in FIG. 2D. Thus, when the arms are brought closer together one or more of the convex areas on the internal surface of one panel can abut against one or more convex areas on the internal surface of the opposite panel. This can cause to be formed one or more ducts 58 between the concave areas on the internal surface of the panels. The external surface 54 on each panel against which the pressure infusion cuff 8 presses can likewise have both concave and convex areas. In a further alternative embodiment, the surface against which the pressure infusion cuff presses is flat and has minimal or no curvature. FIG. 2D illustrates a non-limiting example of a collar having one panel with two or more concave areas and two or more convex areas on both the internal surface and the external surface and another panel that has two or more concave and convex areas on the internal surface and an external surface that is substantially flat.

Embodiments of a clip collar 10 employ at least two arms 30 that can be configured so as to be placeable around a fluid bag, such that the arms are in contact with a front and back surface of the fluid bag and can encircle or "clip" over all or most of the fluid bag. Alternatively, the arms can partially encircle or clip over the fluid bag. FIGS. 1A and 1B and 8B and 8C illustrate non-limiting examples of clip collar embodiments that can clip over and along the vertical sides 6 of a fluid bag. FIG. 8A illustrates one example of this embodiment utilized on a fluid bag.

In one embodiment, the arms of a clip collar 10 are operably connected along one hinged edge 38 to form an articulating side 40. The articulating side, where the arms are moveably joined, allows the arms to be folded together, similar to a book cover, so that a closing side 60 is formed by the side edges coming together. As discussed above, this provides a channel 70 with a direction that is parallel to the articulating side and/or the closing side 60, which is illustrated in FIGS. 1A and 8A. With this embodiment, the clip collar 10 can be placed around a fluid bag 5 and the fluid bag and clip collar 10 placed within a pressure infusion cuff 8. As the pressure infusion cuff is expanded the interior walls of the cuff will press against the outer convex surfaces 36 of the at least two arms. The articulating side 40 will allow the arms to fold together bringing the side edges 32 closer together to form a closing side 60. This can cause a channel 70 to be formed between the concave surfaces, when the arms come together on the closing side. When the closing side is formed by the evacuation of sufficient fluid from the fluid bag, the channel 70 formed between the arms will prevent the fluid bag from being further compressed by the cuff 8 and will encompass a volume sufficient to prevent an air pocket in the fluid bag from being compressed. Advantageously, the formation of the channel does not interfere with the continued evacuation of the fluid, which continues to be facilitated by gravity force. FIGS. 1A through 2B illustrate non-limiting examples of clip collar 10 embodiments.

In an alternative embodiment, a clip collar can be configured to be placed over one end, for example, the distal end, of a fluid bag. This alternative embodiment can employ arms having a curvature or concave side that is rotated 90 degrees from the clip collar position, such that the curvature is between the top edge 31 and the bottom edge 33. The change in direction of curvature would further allow the top edge and the bottom edge to come together when the arms are rotated on the articulating edge, such that the top and bottom edges become equivalent to side edges. This could provide two closing sides 60. This can further change the direction of the channel 70 so as to be parallel with the top edge and the bottom edge, and thus perpendicular to the articulating side 40. FIGS. 21A, 21B, and 21C illustrate one example of this alternative embodiment and FIG. 21C illustrates how the change in channel direction allows this clip collar embodiment to be placed over an end, here the distal end 4, of a fluid bag, so that it "caps" the end of the fluid bag. For literary convenience, the clip collar will be discussed herein and the cap collar alternative will be referred to when necessary for clarification. Thus, it will be understood that the features and alternatives described herein for a clip collar are equally applicable to the alternative cap collar embodiment, unless stated otherwise.

The volume encompassed by the channel 70 of a clip collar can be between approximately 20 cc and approximately 350 cc. More specifically, the volume encompassed by the channel can be between approximately 100 cc and approximately 300 cc. Still more specifically, the volume encompassed by the channel can be between approximately 125 cc and approximately 175 cc. In a particular embodiment, the volume encompassed by the channel is about 150 cc.

The articulating side 40 of a clip collar 10 can allow the arms to rotate towards and away from each other so that the clip collar can be placed around a fluid bag and the arms can come together as the fluid bag is emptied. The distance or angle that the arms need to rotate can depend upon the width of the fluid bag when full. It can also depend upon the depth of the concave surfaces. It can be beneficial for any one embodiment of the subject invention to be useful on multiple sized or different shaped fluid bags. Thus, for clip collar embodiments, the distance that the arms can rotate should be sufficient to allow the clip collar 10 to encircle or at least be placed partially around a fluid bag 5. In one embodiment, the articulating side 40 of a clip collar 10 allows the two or more arms 30 to be separated, such that an angle formed between the concave surfaces 34 is anywhere between 0° and 360°. More specifically, the angle formed between the two or more arms is at least 5°, 10°, 15°, 20°, 25°, 30°, 35°, 40°, 45°, 55°, 60°, 65°, 70°, 75°, 80°, 85°, 90°, 95°, 100°, 105°, 110°, 115°, 120°, 125°, 130°, 135°, 140°, 150°, 155°, 160°, 165°, 170°, 175°, 180°, 185°, 190°, 195°, 200°, 205°, 210°, 215°, 220°, 225°, 230°, 235°, 240°, 250°, 255°, 260°, 270°, 275°, 280°, 285°, 290°, 295°, 300°, 305°, 310°, 315°, 320°, 325°, 330°, 335°, 340°, 345°, 350°, 355° and/or an angle in a range between any two of the listed values. The required range of rotation for two or more arms can be determined by a person having skill in the art. Such variations are within the scope of this invention.

There is a variety of techniques that can be employed with embodiments of a clip collar 10 to configure an articulating side 40. In one embodiment, a hinge system can be used, such as shown, for example, in FIGS. 4A, 4B, 5A and 5B. With this embodiment an interlocking side can be configured with one or more interlocking hinge knuckles 46, which are shown by way of example in FIGS. 4A and 6A. The knuckles can be rotatably held together with a pin through a center shaft in each knuckle.

In another embodiment, a flexure bearing hinge, a.k.a., a living hinge, can be employed between the two or more arms on the articulating side of a clip collar 10. A flexure bearing is a structure that allows motion between two or more elements by bending of a flexure element 48. The flexure element, such as, for example, a flexible piece of material, is positioned between the two parts that need to rotate. Oftentimes, though not necessarily, a flexure element 48 is made of the same material as the parts that need to rotate, except that it is made thinner or more pliable in that specific area, allowing the material to flex. In one embodiment, a flexure bearing is fixedly attached to two side edges between two or more arms of a clip collar. FIGS. 2C and 21A-21C illustrate examples of a flexure bearing connected between two arms. The flexure bearing can allow the arms to rotate and for the one or more closing sides 60 of the arms to be formed when the two or more side edges 32 are brought together. It can also have sufficient rigidity, be biased, or have a pre-defined shape that helps to keep the arms substantially aligned when they are brought together. Hinge systems are well-known in the art and there are multiple types and configurations that can be used with the clip collar embodiments of the subject invention. Such variations that provide the same function, in substantially the same way, with substantially the same result are within the scope of this invention.

On a clip collar 10 that utilizes two or more arms 30, the side edges 32 that come together to create a closing edge 60 of the arm can be opposite to the articulating side 40 on an arm and can also be those sides where the arms of the clip collar come together as the arms rotate on the articulating side 40. As mentioned above, a clip collar can be configured as a cap collar, in which the side edges that come together are perpendicular to the articulating side 40 or the hinged edge 38 on each arm.

Figure 1B:
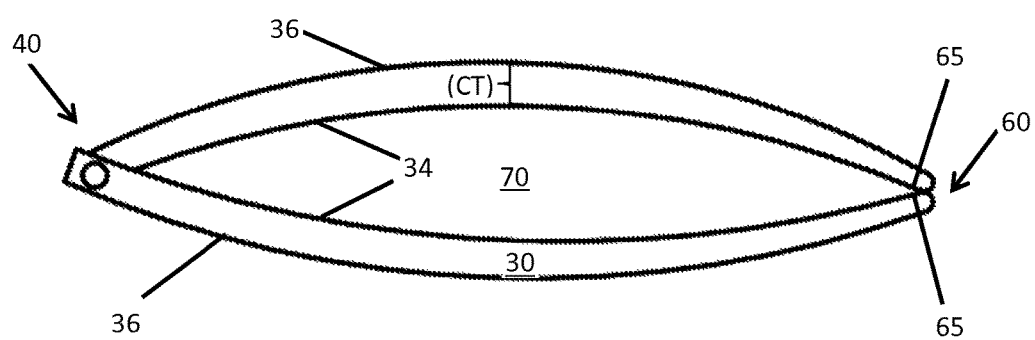
FIG. 1B is a proximal end elevation view of an embodiment of a collar, according to the subject invention. This embodiment shows arms of the same length.

In one embodiment, a side edge has a facing edge 65, which is a surface or area where the side edges come closer together and/or make contact. These facing edges on each arm can meet or come into close proximity at the same point or position on each arm. In another embodiment, the dimensions of the arms allow the side edges to substantially align, so that they terminate at the same point and their facing edges are at similar locations on each arm. By way of non-limiting example, the facing edges on each arm can be mirror images of each other or could have complementary structures that allow them to interdigitate in some fashion. FIGS. 1B and 21A illustrate non-limiting examples of this type of clip collar embodiment. Alternatively, the dimensions of the arms can cause the closing side 60 to be misaligned, where one side edge 32 of an arm terminates before the side edge of the opposite arm, e.g., one arm can be shorter than the other, which is shown, by way of non-limiting example, in FIG. 2B. Further, the facing edges 65 on the side edges 32 can be located at any point at or about the side edges on the closing side of a clip collar 10. The side edges on the closing side do not necessarily have to touch, but can be brought adequately close together to achieve the formation of a channel 70. FIG. 1B illustrates an example of a clip collar where the side edges on each arm come together and make contact. FIG. 2B illustrates an example of a clip collar where the side edges on the closing side on each arm come together adequately to form a channel between them, but their facing edges do not actually make contact. FIGS. 21A-21C illustrate a particular cap collar embodiment, an embodiment similar to a clip collar, where the side edges are configured to align along a flat edge. In an alternative embodiment, the facing edges on a cap collar have interdigitating surfaces 66, such that the facing edges are not flat surfaces, but have a surface that is waved, dimpled, indented, ridged, or any of a variety of other surface forms or extended surface features that are known to those with skill in the art. FIG. 8C illustrates one example of an interdigitating surface 66 that could also be employed with a clip collar.

In certain embodiments, which will be discussed below, the air pocket in a fluid bag can be captured and/or contained by the channel 70, as the fluid bag is evacuated. One or more sealing edges, as described below, can be used to ensure that the air pocket remains within the channel. In order to further ensure that the air pocket in the fluid bag is contained and that the air is not susceptible to being compressed by a pressure infusion cuff 8, it can be advantageous for the closing side 60 of an arm on a clip collar embodiment to come together as close as possible. In a further embodiment, the facing edges 65 on the side edges 32 have surfaces that facilitate more complete contact or interface between the side edges and/or the facing edges of the arms. Thus, whether the side edges 32 extend past the vertical edge 6 of a fluid bag or do not reach the vertical edge and close over the fluid bag, the facing edges can ensure that there is formed a sufficient closure between the side edges to contain all or at least part of the air pocket.

As mentioned above, it is not required that a clip collar extends fully from one vertical side to another of a fluid bag or that 100% of the air in the bag be contained. As long as the dimensions of a clip collar allow it to capture or contain at least 30%, 35%, 40%, 45%, 50%, 55%, 60%, 65%, 70%, 75%, 80%, 85%, 90%, 95%, and/or 99%, and/or an amount in a range between any two of the listed values, any uncaptured air will also be inhibited from entering the IV tubing, due to the decreased pressure on the bag by the presence of the collar. Thus, it will be understood by the skilled artisan, that the width (W) and height (H) of the arms of the collar can vary considerably depending upon these and other factors.

Figure 8B:
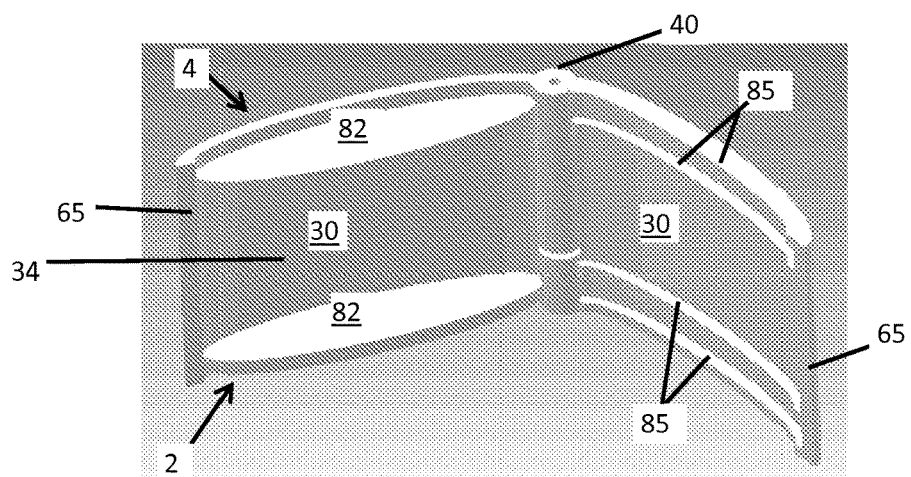
FIG. 8B is a proximal end perspective view of a collar embodiment having dual seals.
Figure 8C:
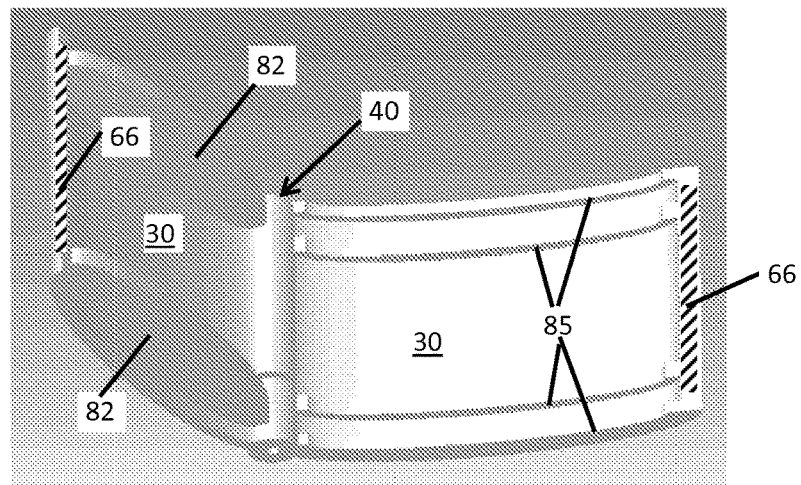
FIG. 8C is a distal end perspective view of the collar embodiment in FIG. 8B.
Figure 8D:
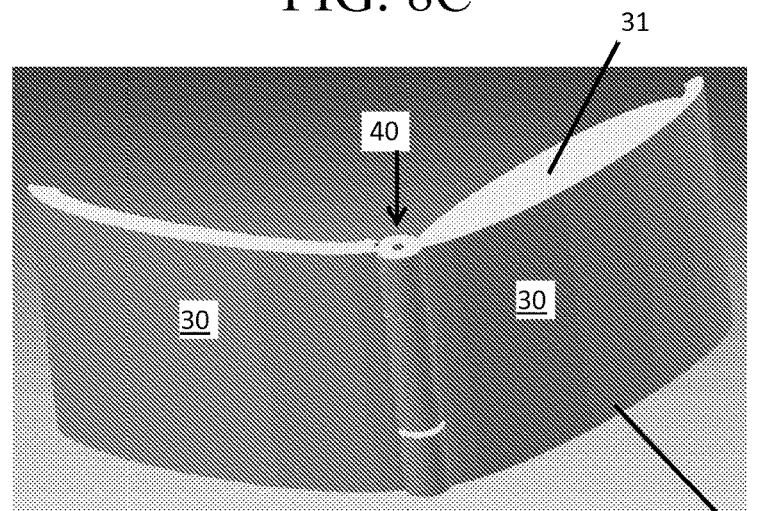
FIG. 8D is a perspective view of the convex surfaces of a collar embodiment.
Figure 10A:
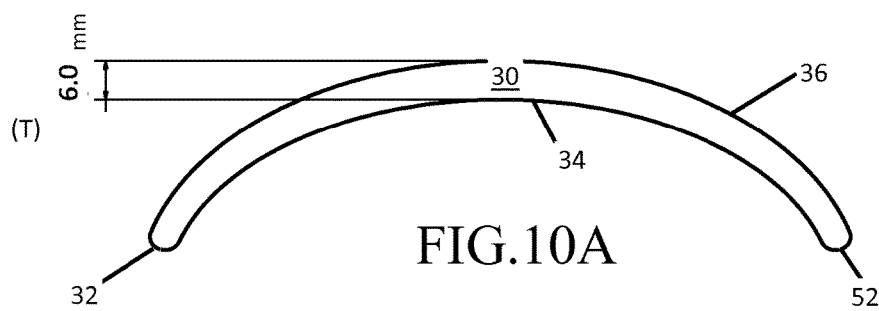
FIG. 10A is a distal end elevation view of an embodiment of a single-arm collar.
Figure 10B:
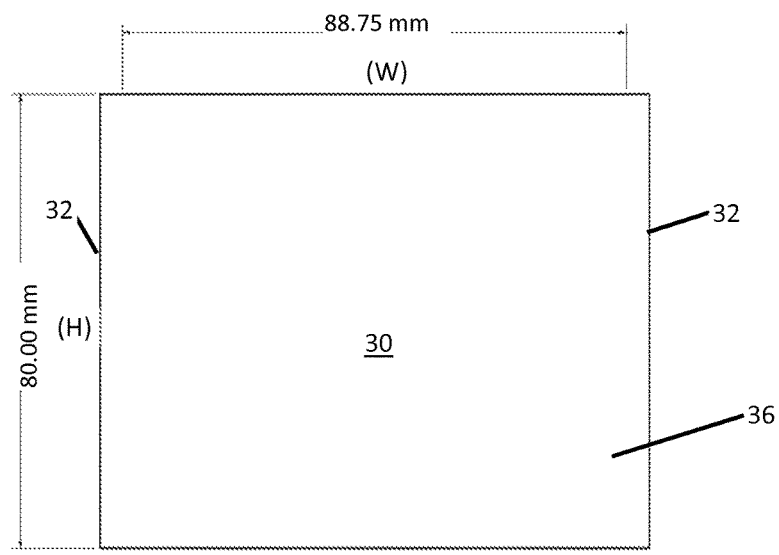
FIG. 10B is an elevational view of the convex side of a single-arm collar.
Figure 10C:
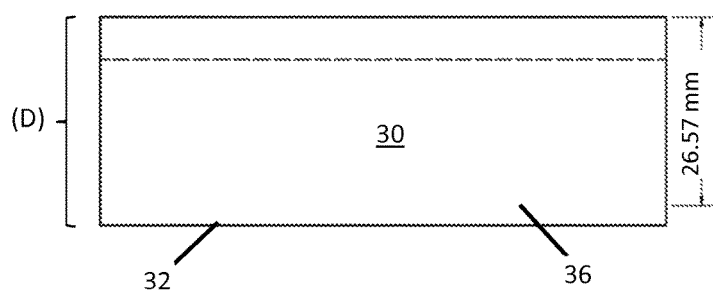
FIG. 10C is an elevation view of a side edge of a single-arm collar.
Figure 10D:
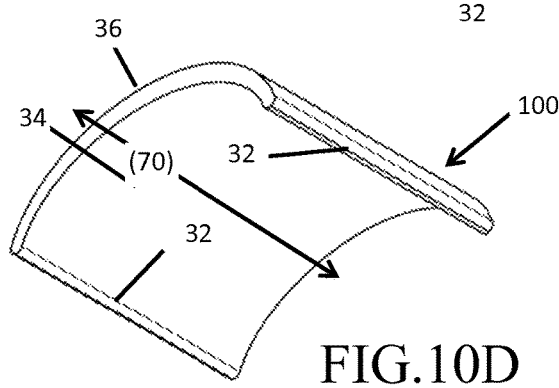
FIG. 10D is a perspective view of the concave surface of a single-arm collar.

In one embodiment, a facing edge 65 has a flat surface, which is shown, by way of non-limiting example, in FIGS. 8A, 8B, and 8C. When two or more facing edges make contact, these flat surfaces can provide more contact surface area. In an alternative embodiment, the facing edges have interdigitating surfaces, such that the facing edges are not flat surfaces, but have a surface that is waved, dimpled, indented, ridged, or any of a variety of other surface forms or extended surface features that are known to those with skill in the art. FIG. 8C illustrates one example of a facing edge having an interdigitating surface.

The embodiments described above can inhibit the air pocket in a fluid bag from being compressed by a pressure infusion cuff. This can further prevent air from being forced into the IV tubing where it may be infused into a patient. Given the potential fatal effects of infusing air into a patient, it can be beneficial for the collar embodiments of the subject invention to adequately isolate an air pocket to ensure that air does not reach the IV tubing.

A clip collar 10 that utilizes two or more arms can further include one or more seals 80 that can further aid in isolating an air pocket within the channel 70. FIGS. 2A and 2B illustrate an embodiment of an elongated blade seal 82 extending from at or about one side edge 32 to at or about the opposite side edge 32 of one arm 30 and a sheathing edge 84 that likewise extends from at or about one side edge to at or about the opposite side edge of another arm. When the arms are brought together, as described above, the sheathing edge and the blade seal traverse the channel, so that the blade seal can fit into or against the sheathing edge to form a bend or constriction over the fluid bag or portion thereof within the channel, which can inhibit air in the fluid bag from moving past the seal. FIG. 2A illustrates an embodiment where the sheathing edge on one concave surface 34 has "V"-shaped sheathing walls 85 that can receive a compatibly shaped blade seal located on the opposite concave surface 34, as illustrated for example in FIG. 2B. FIGS. 3A-5B illustrate details of this embodiment. FIGS. 8A-8C illustrate a similar embodiment where the blade seal 82 and the sheathing edge 84 have a different configuration, but operate in the same manner, in that the sheathing edge 84 receives the blade seal 82 between two compatibly configured sheathing walls 85.

The embodiment shown in FIGS. 8A-8C illustrates how embodiments of a collar 9 can have more than one seal 80. In this embodiment, a clip collar has a seal at about the distal end 4 and another seal at about the proximal end 2. Additional seals could be employed if it was deemed necessary. In addition, different types of seals could be used in different areas of a collar embodiment, whether a clip collar, as described above, or on rigid collar embodiments, described further below. Still further, two or more seals can be configured on embodiments of a collar 9, so that they close over the fluid bag simultaneously or, alternatively, so that one seal closes over the fluid bag at a different time or at a different rate than another seal. By way of example, the blade seal and/or the sheathing edge at the proximal end of a clip collar could be larger than the blade seal and/or the sheathing edge at the distal end of a clip collar. As the pressure infusion cuff pushes the arms of the collar together, the proximal seal will close and seal off the fluid bag prior to the seal at the distal end. The seals could also be reversed on a collar so that the distal end seal closes and seals the bag prior to the seal at the proximal end.

The one or more components of a seal, e.g., the blade seal and/or the sheathing edge, can follow the curvature of the concave surface of an arm. Alternatively, they can extend away from the concave surface so that they do not conform to or do not conform entirely to the curvature of the concave surface. FIGS. 3A and 3B and 5A and 5B illustrate a clip collar embodiment where the blade seal and the walls 85 of the sheathing edge on each of the arms extend out or away from the concave surfaces so that the edges where they meet are generally linear relative to the concave surfaces to which they are affixed. Alternatively, one or more of the seal components could also extend out from the concave surface and another component on the opposite arm could be recurved, linear or some combination thereof, such that the components have different configurations relative to the concave surfaces, but where the seal components can still compatibly come together.

In an alternative embodiment, only a blade seal 82 is used for a seal 80 on a collar embodiment. In a clip collar embodiment that uses two or more arms, a blade edge can be configured to have a shape that conforms to the shape of the concave surface of an opposite arm. When the arms come together, the blade edge on one arm can abut against the concave surface of the opposite arm, compressing the fluid bag at the point where the concave surface and the blade edge intersect. The embodiment shown, for example, in FIGS. 8A, 8B, and 8C illustrate this embodiment. With this embodiment, the sheathing walls 85 could be eliminated and the curved shape of the blade edge would allow it to abut against the concave surface of the opposite arm. Thus, the concave surface of one arm can act similarly to a sheathing edge for a blade seal. A fluid bag in the channel 70 therebetween would be constricted where the blade edge meets the concave surface of the opposite arm.

Figure 3A:
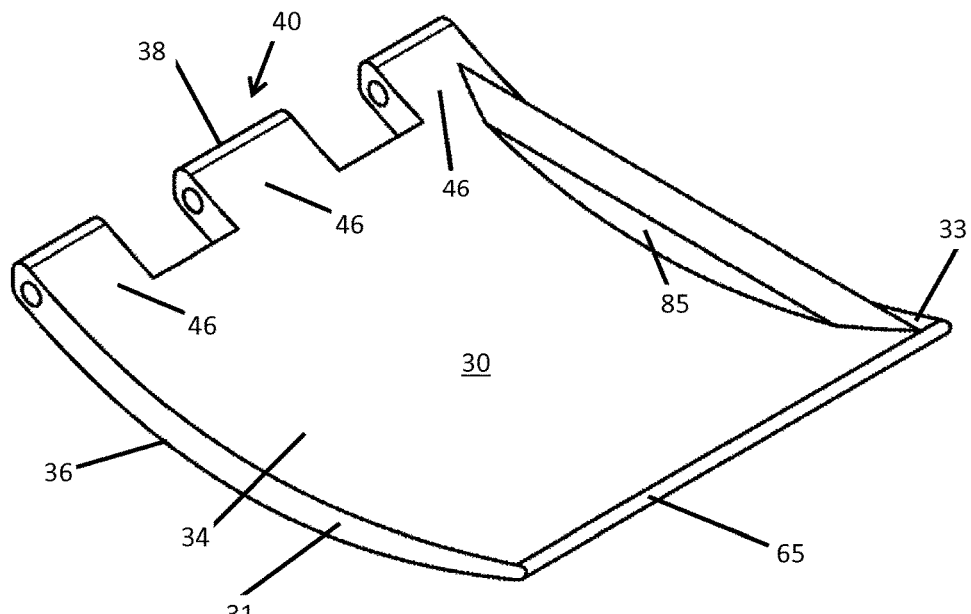
FIG. 3A is a distal end perspective view of the concave interior surface of one embodiment of an arm having a blade edge, according to the subject invention.
Figure 3B:
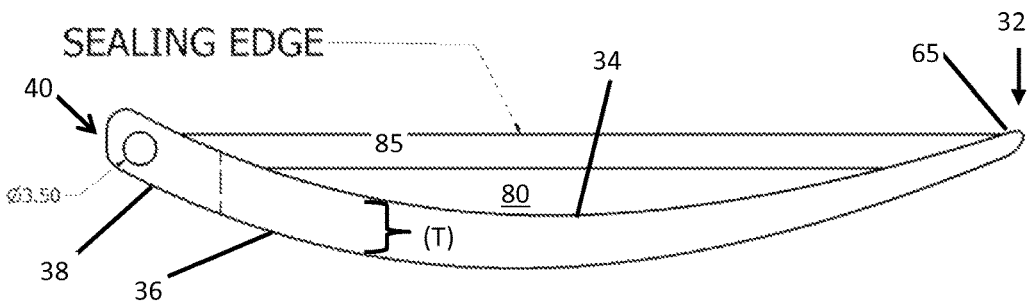
FIG. 3B is a proximal end elevation view of an embodiment of the arm embodiment shown in FIG. 3A.
Figure 3C:
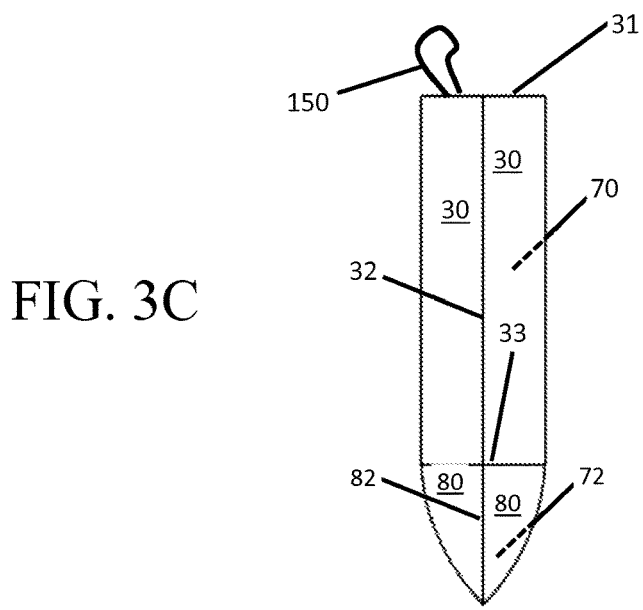
FIG. 3C is an elevational view of the side edges of a collar, where the arms have a dome-like seal. This view shows how the side edges and the seals align to create a cup-like interior. Also shown is a hanger loop.
Figure 4A:
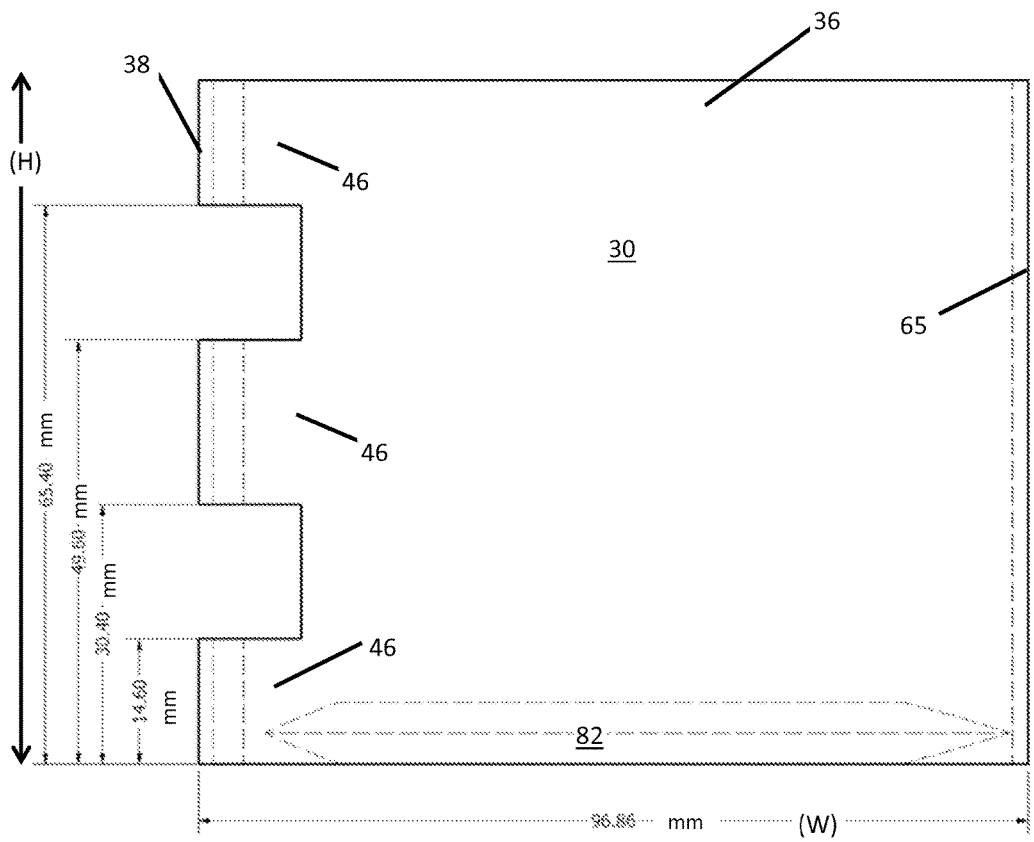
FIG. 4A is an elevational view of the convex surface of an arm having a knuckle hinge articulating side and a blade edge (shown in dashed lines), according to the subject invention.
Figure 4B:
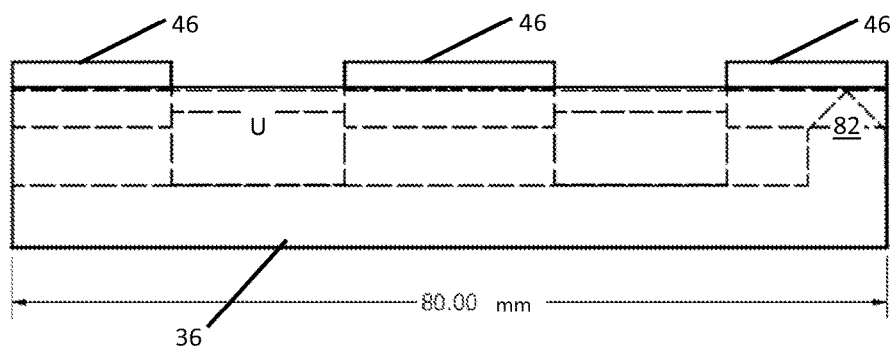
FIG. 4B is an elevation view of the articulating side of the arm shown in FIG. 4A.
Figure 5A:
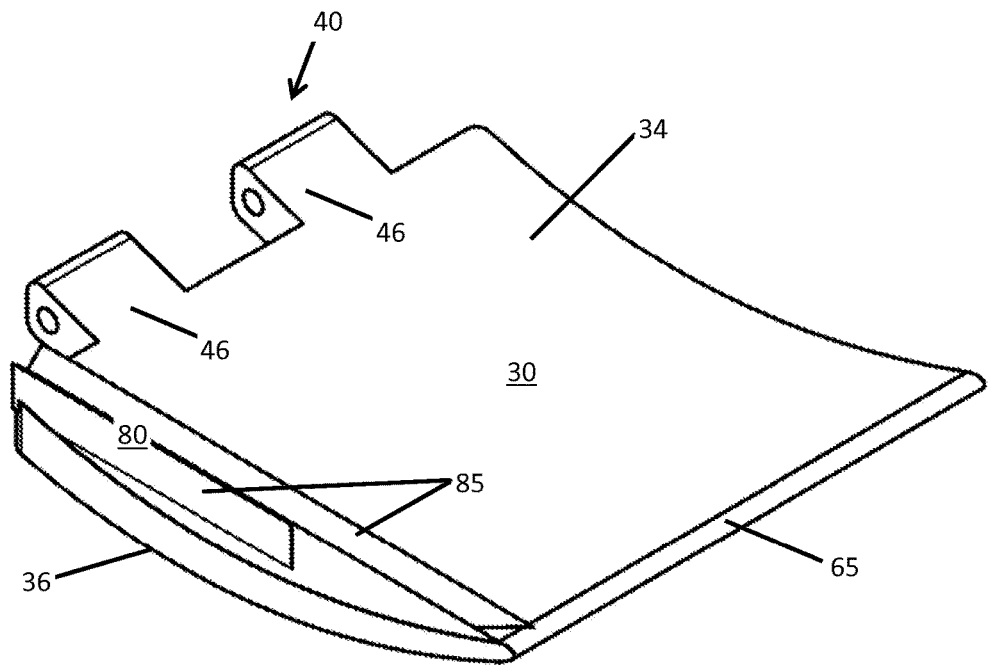
FIG. 5A is a proximal end perspective view of the concave interior surface of one embodiment of an arm having a sheathing edge, according to the subject invention.
Figure 5B:
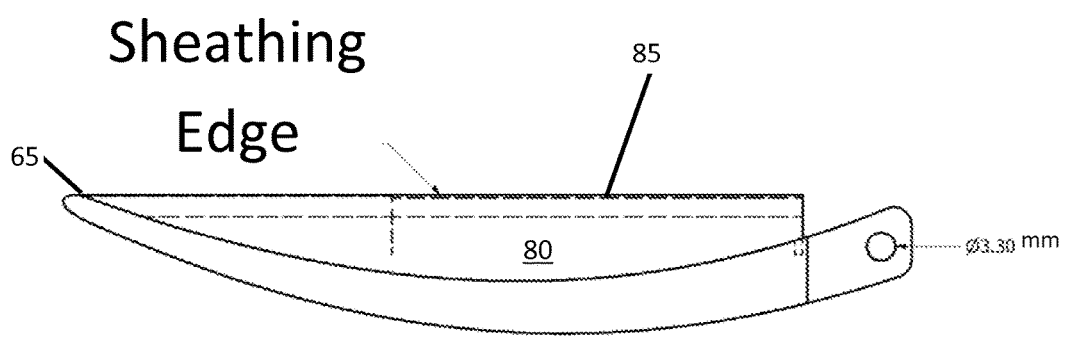
FIG. 5B is proximal end elevation view of the arm embodiment shown in FIG. 5A.
Figure 6A:
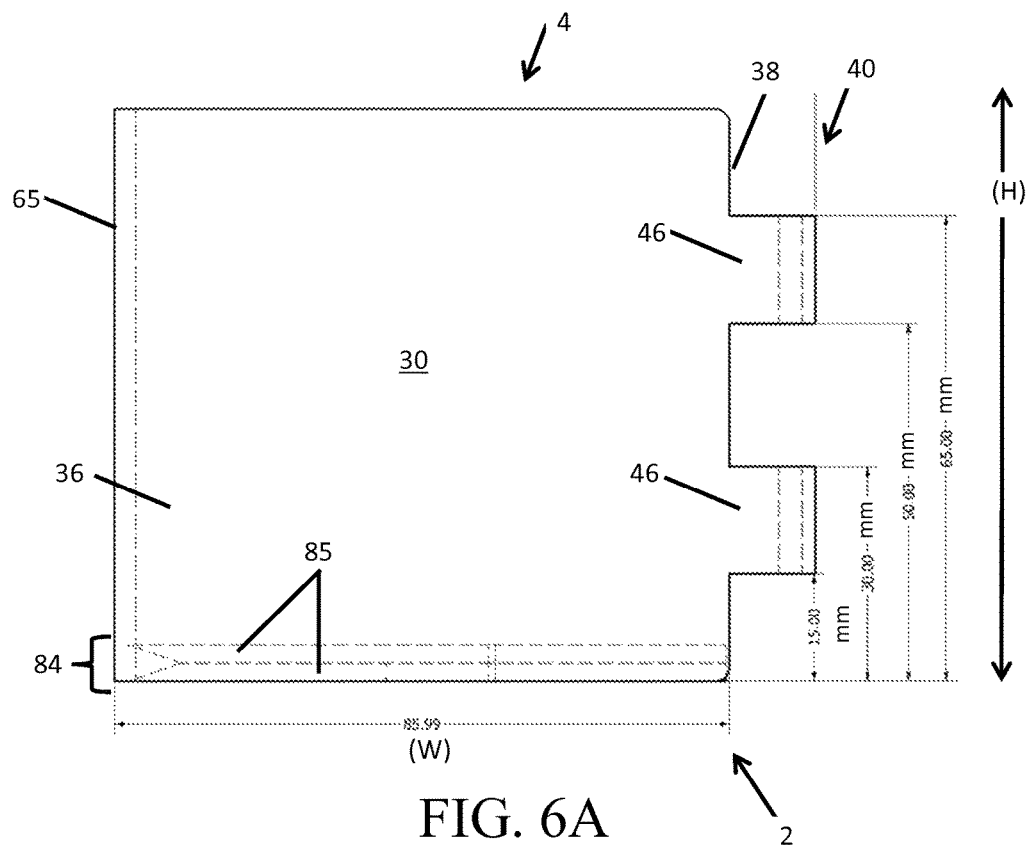
FIG. 6A is an elevational view of the convex surface of an arm having a knuckle hinge articulating side and a sheathing edge (shown in dashed lines), according to the subject invention.
Figure 6B:
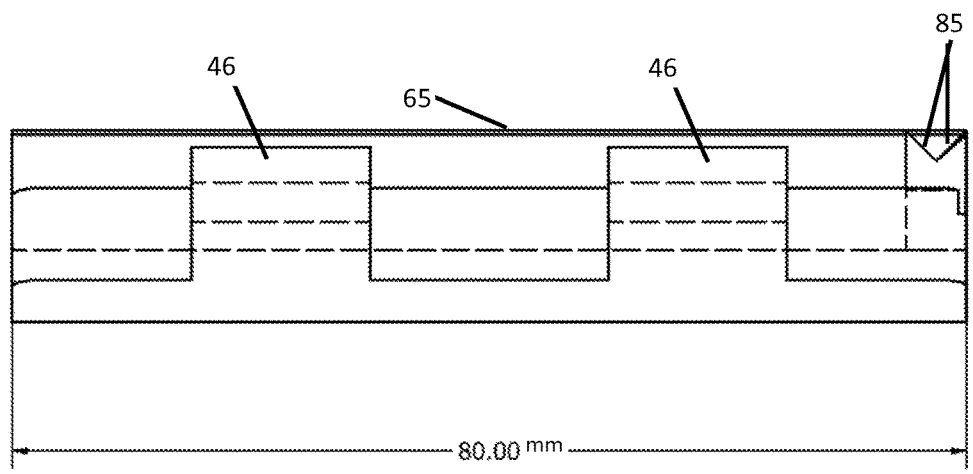
FIG. 6B is an elevation view of the articulating side of the arm shown in FIG. 6A.

In an alternative embodiment, a seal is a rigid extension 86 from the proximal end 2 of an arm 30 embodiment of the subject invention. This proximal rigid extension seal can be similar to an embodiment of a blade seal 82 described above, except that a rigid extension seal extends past the proximal end of an arm embodiment of the subject invention and has a scooped shape that forms a depression or void 87 at the proximal end of the arm. With this embodiment, the blade seal 82 can extend away from the proximal end of an arm embodiment for a predetermined distance and then recurve or bend towards the concave surface 34 and the side edges, so that a lip 88 of the rigid extension seal can be contiguous with the side edges 32 of an arm embodiment. In certain embodiments, the lip 88 of a rigid extension seal does not extend beyond the side edges 32, as illustrated in FIG. 3C, such that when the arms are brought together and the side edges make contact, the lips of each rigid extension seal on an arm also come together so that the two voids 87 form a cup-like cavity 72 below the channel 70 when the arms come together, which is illustrated, for example, in FIG. 3C. FIGS. 11A-12D further illustrate non-limiting examples of a rigid extension seal embodiment, where the void is semi-spherical. It will be understood by a skilled artisan that a void 87 and any depression or cup-like cavity 72 formed by a void can have any desirable shape, such as partially-spherical, as shown, to more squared, oval, or even cone-like in shape. Such variations in the shape of a void and/or the cup-like cavity 72 are within the scope of this invention.

As shown in the above-described embodiments, a seal can be used to contain an air pocket in an IV fluid bag within the channel 70 of a collar. There can be more than one seal on a collar. A seal can also have components on one or more arms of a collar, where the components can be compatibly connected. Embodiments of a collar 9 that have two arms can have components, such as the blade edge and the sheathing edge, on opposite arms that engage when the arms are brought together. A collar embodiment with two arms can also have one or more components, such as a blade edge, on one arm that aligns with or conforms to the concave surface shape on an opposite arm. A seal would not be required to contain or isolate all of the air in the fluid bag, but can isolate or contain a sufficient amount so that the collar inhibits the pressure infusion cuff from acting on any uncontained air that may be in the fluid bag and forcing it into the IV tubing. A person skilled in the art, having benefit of the subject disclosure, would be able to determine any of a myriad of seal configurations that could constrict, bend, or otherwise seal an IV fluid bag so that air therein is inhibited from being forced by a pressure infusion cuff into the IV tubing. Such variations are within the scope of this invention.

A particular embodiment of a clip collar of the subject invention is illustrated in FIGS. 4A, 4B, 6A and 6B. This particular embodiment has two arms 30 that have articulating sides 40 and two or more closing sides 60, where the arms further have concave surfaces 34 that come together to form a channel 70 between them. In a more specific embodiment, the arms are of different lengths, causing them to be offset, such that the closing side of one arm terminates prior to the closing side of the opposite arm, such that their facing edges 65 are located in a different position on each arm. With this embodiment, the facing edges may not be mirror images of each other, as described above. In this particular embodiment, the width (W) of the longer arm is between approximately 95 mm and approximately 100 mm between the closing side and the articulating side (not including the hinge system or other rotational elements). In a further particular embodiment, the width (W) of the shorter arm is between approximately 84 mm and approximately 88 mm between the closing side and the articulating side (not including the hinge system or other rotational elements). The height (H), between the proximal end and the distal end of each arm, can be between approximately 50 mm and approximately 100 mm.

An alternative collar 9 embodiment of the subject invention is a rigid collar 100 that utilizes a single arm 30 having a configuration that allows it to inhibit air within an IV fluid bag from being compressed into the IV tubing by a pressure infusion cuff 8. As described above, an arm can have a concave surface 34 and an opposing convex surface 36. The considerations with regard to the size and/or dimensions of an arm have been discussed above with regard to embodiments that utilize two or more arms. Those considerations are also applicable to rigid collar embodiments that employ a single arm and are reiterated here with respect to the single arm of rigid collar embodiments. In addition, the factors that can be considered by those skilled in the art with regard to the choice of materials for each of the components of the subject invention have been discussed above and are reasserted here with regard to the rigid collar embodiments of the subject invention.

The single-arm rigid collar 100 embodiment can be positioned with the concave surface against one side of an IV fluid bag 6, as shown, for example, in FIGS. 9A-9C and 22B and 22C. The IV fluid bag and the rigid collar can then be placed within a pressure infusion cuff. As the pressure infusion cuff presses against the IV fluid bag and the convex surface 36 of the rigid collar, the IV fluid bag empties and collapses against the concave surface 34 of the arm 30 of the rigid collar 100. When the IV fluid bag empties sufficiently, the interior side of the pressure infusion cuff will encounter the side edges 32 of the rigid collar. The rigidity of the rigid collar, which is discussed above, including the side edges, can inhibit the pressure infusion cuff from continuing to press against that portion of the fluid bag that collapses into the concave surface. The fluid remaining in the bag will continue to drip out, facilitated by gravitation force. However, the rigid collar will inhibit the pressure infusion cuff from squeezing the fluid bag to the point where air in the bag will be forced into the IV tubing after all of the fluid is drained out of the bag. Thus, the inside of a pressure infusion cuff and the concave surface of the rigid collar create a channel 70 in which the fluid bag is protected against full compression, similar to the clip collar 10 embodiment described above that employs two or more arms.

While the dimensions of a single-arm rigid collar can vary, it can be most advantageous for the dimensions to allow it to be used with IV fluid bags of multiple sizes. By way of example, a rigid collar can have a width (W), from one side edge 30 to the other side edge, of between approximately 75 mm to approximately 100 mm. The depth (D) of the channel 70 formed can be between approximately 25 mm to approximately 35 mm. The height (H) of the rigid collar can be between approximately 75 mm and approximately 85 mm.

The width (W) of a rigid collar can be sufficient that it extends along one side, either the front of back, of an IV fluid bag 5. The width of a rigid collar can allow the side edges 32 to extend to the vertical edges 6 of the fluid bag, such as shown, for example, in FIGS. 9A-9C. Alternatively, the width can be less, such that the side edges 32 do not reach all the way to the vertical edges 6 of a fluid bag. It is not required that a rigid collar contain 100% of the air in the fluid bag. As long as the dimensions of a rigid collar allow it to capture or contain at least 30%, 35%, 40%, 45%, 50%, 55%, 60%, 65%, 70%, 75%, 80%, 85%, 90%, 95%, and/or 99%, and/or an amount in a range between any two of the listed values, any uncaptured air will also be inhibited from entering the IV tubing, due to the decreased pressure on the bag by the presence of the collar. Fluid will continue to evacuate from the bag under gravitation force. Thus, it will be understood by the skilled artisan, that the width (W) and height (H) of the arms of the collar can vary considerably depending upon these and other factors.

Figure 22A:
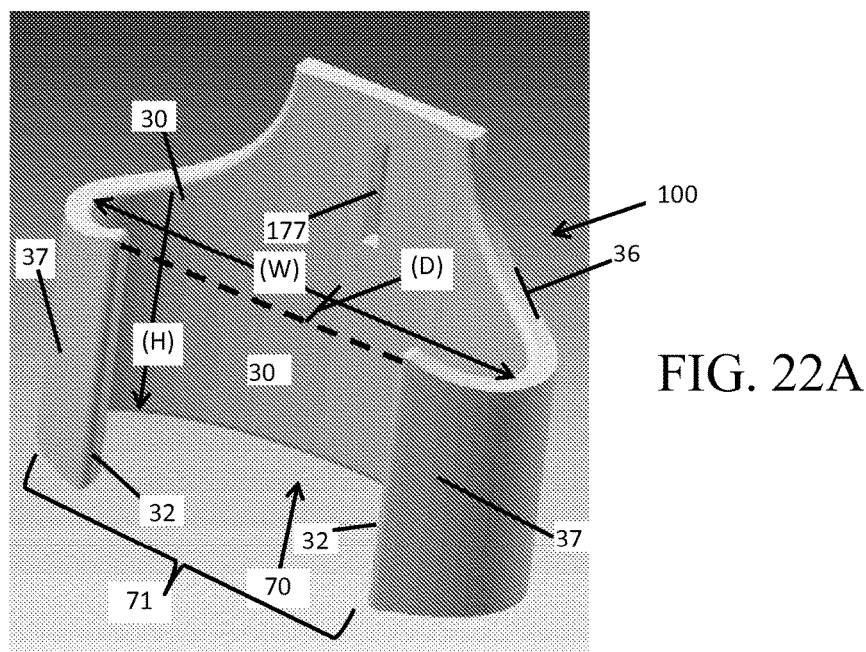
FIGS. 22A, 22B, and 22C illustrate embodiments of a rigid collar with wings, where
Figure 22B:
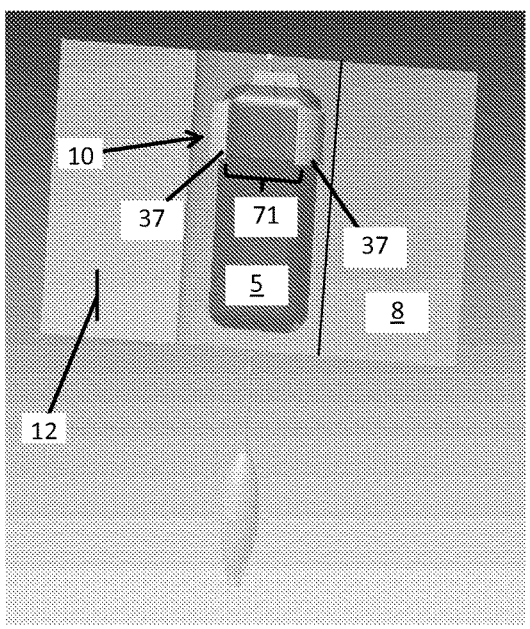
Figure 22C:
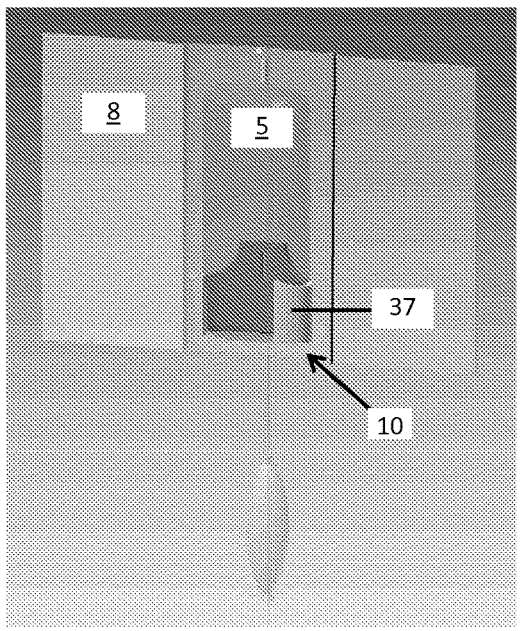
Figure 23A:
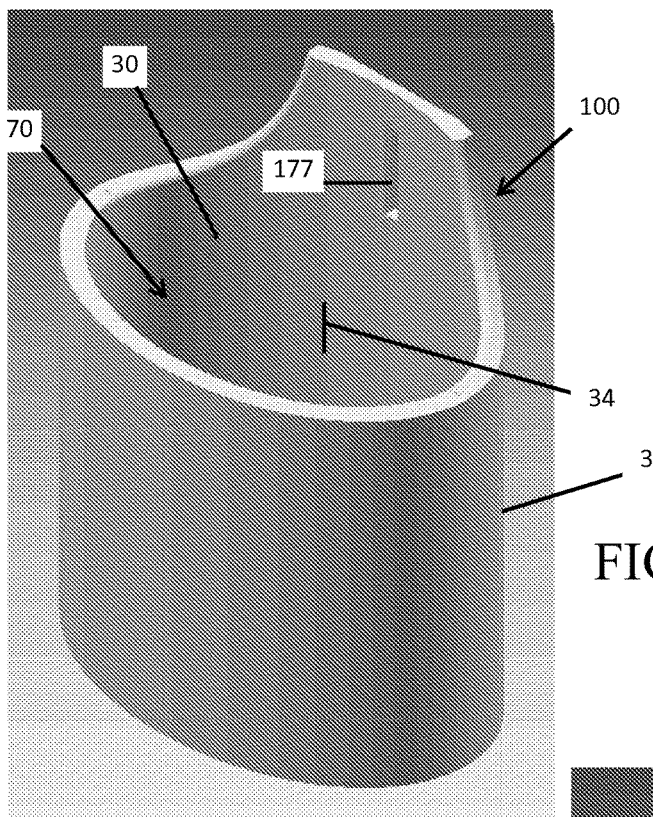
FIGS. 23A and 23B show an embodiment of a rigid collar wherein the wings or side edges are joined.
Figure 23B:
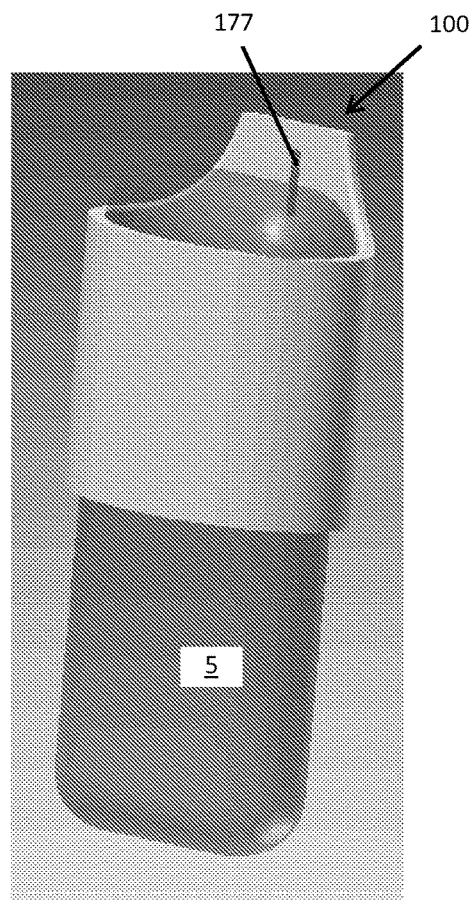

In an alternative embodiment, the side edges 32, concave surface 34, and the convex surface 36 of a rigid collar extend around or recurve around causing the side edges to form wings 37 where the side edges are directed towards, or even facing, each other. When positioned on a fluid bag, the wings at least partially cover the side of the fluid bag opposite of the one against which the rigid collar is placed. Thus, when the rigid collar is placed against a fluid bag, the wings go around the vertical edges 6 of the fluid bag. FIGS. 22A, 22B and 22C illustrate a non-limiting example, where the rigid collar is placed along one side, such as the back, of a fluid bag and the wings 37 extend around to the other side, such as the front, of the fluid bag. With this embodiment, the wings inhibit the fluid bag from being pinched between the side edges and the pressure infusion cuff as the fluid evacuates the bag. With this embodiment, the wings recurve towards each other, but do not meet, which can also provide an entry way 71 through which a bag can be inserted into the channel 70.

In another alternative embodiment, the side edges 32, concave surface 34, and convex surface 36 recurve completely around, so that the side edges 32 abut, overlap, connect, or otherwise eliminate the entry way 71. This can provide a tube-shaped rigid collar with a central tubular channel 70, such as shown, for example, in FIGS. 23A and 23B. When positioned on a fluid bag, this embodiment of a rigid collar will go around the vertical sides 6, encircling a fluid bag, so that it covers at least part of both sides of a fluid bag, as shown in the example in FIGS. 23A and 23B. This embodiment provides the unique advantage of being more easily used with pressure infusion cuffs that are also tubular.

This embodiment of a rigid collar can be placed around a fluid bag and the rigid collar and fluid bag can be simultaneously slid into the tubular pressure infusion cuff. Other infusion cuff embodiments can be laid open or placed flat on a surface and the rigid collar with the fluid bag therein and the pressure infusion cuff closed thereover. By way of further example, the channel 70 formed by any of the embodiments of a rigid collar 100 and a pressure infusion cuff can encompass or contain approximately 20 cc to approximately 350 cc of air within a fluid bag. More specifically, the volume of air in a fluid bag that can be encompassed by the channel 70 can be between approximately 100 cc and approximately 300 cc. Still more specifically, the volume of air within a fluid bag that can be encompassed by the channel can be between approximately 125 cc and approximately 175 cc. In a particular embodiment, the volume of air in a fluid bag that can be encompassed by the channel is about 150 cc. FIGS. 10A-10D, 14, 15, 22A and 23A illustrate rigid collar embodiments having dimensions and a channel volume within these ranges.

As discussed above, an arm 30 can have one or more seals 80 to aid in confining or entrapping air within a fluid bag. In a particular embodiment, shown for example, in FIGS. 11A-12D, a rigid collar can have a rigid extension seal 86 that extends from the proximal end the arm 30 to create a void 87 below the arm, which has been described above. With a rigid collar embodiment, the depression that forms the void can also be an extension of the channel 70, such that a cup-like depression is formed. In the embodiment shown, for example, in FIGS. 11A-12D, a rigid extension seal 86 is utilized with a rigid collar 100. As described above, the interior side of the pressure infusion cuff, when abutted against the side edges 32 of the rigid collar arm, creates a channel 70 with the concave surface 34 in which the deflated fluid bag is protected against excess pressure. With this embodiment, the pressure infusion cuff also presses against the lip 88 of the rigid extension seal 86, as indicated, for example, in FIG. 12B, creating the additional void 87 area below and contiguous with the channel 70. When abutted against a pressure infusion cuff, this creates a cup-like cavity 72, mentioned above, in which the air pocket within a fluid bag 5 can be trapped or contained, inhibiting the air from being forced into the IV tubing.

Figure 12A:
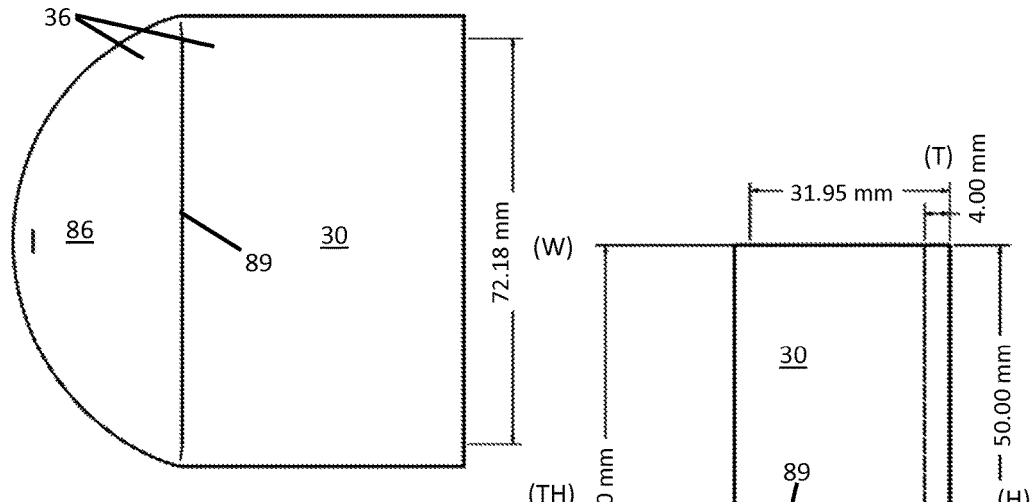
FIG. 12A is a perspective view of a single-arm collar embodiment having a dome-like seal.
Figure 12B:
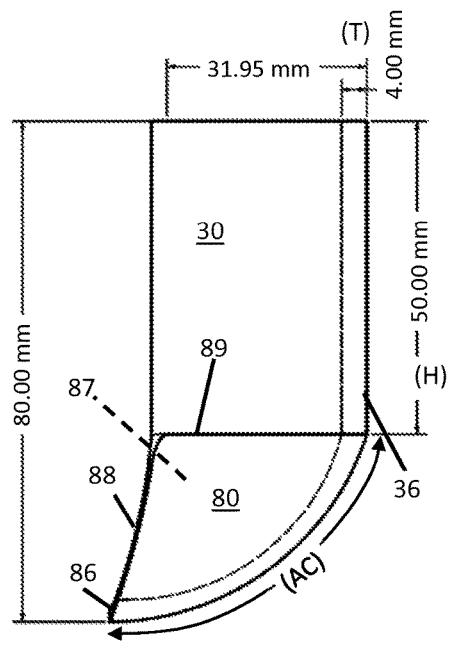
FIG. 12B is an elevational view of a side edge of a single-arm collar embodiment having a dome-like seal.
Figure 12C:
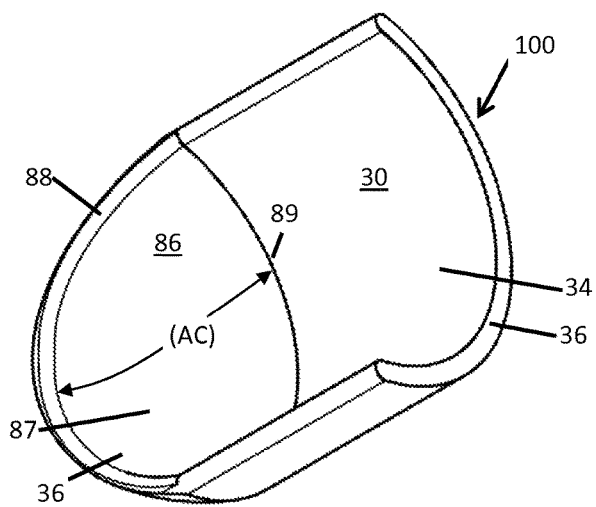
FIG. 12C is a perspective view of the concave surface of a single-arm collar embodiment having a dome-like seal.
Figure 12D:
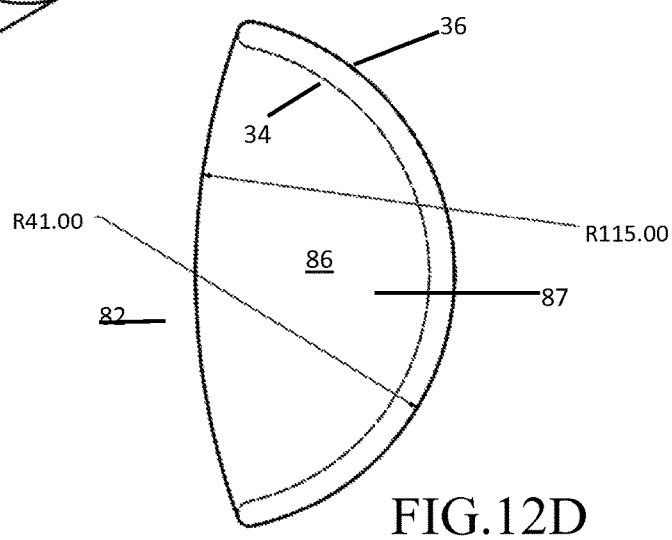
FIG. 12D is a distal end elevation view of a single-arm collar embodiment having a dome-like seal. Note the curvature of the blade edge between the side edges.
Figure 13A:
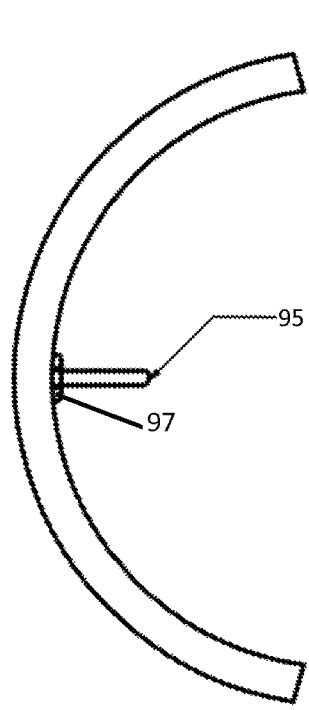
FIG. 13A is a distal end elevation view of a single-arm collar embodiment having a stylet.
Figure 13B:
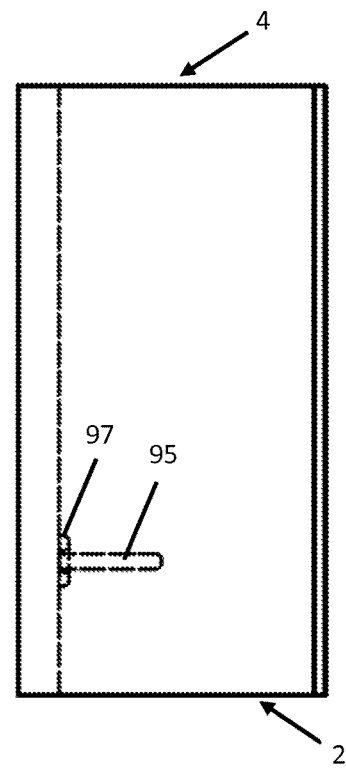
FIG. 13B is an elevational view of a side edge of a single-arm collar embodiment having a stylet.
Figure 13C:
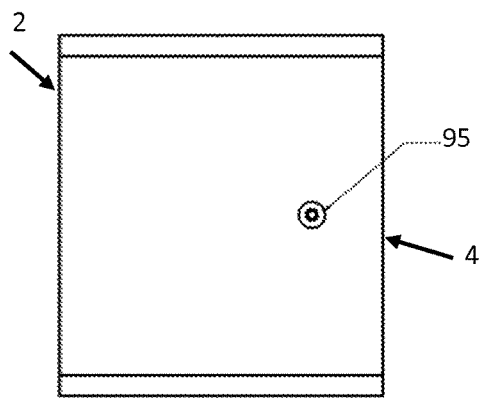
FIG. 13C is an elevational view of the concave surface of a single-arm collar embodiment having a stylet.
Figure 13D:
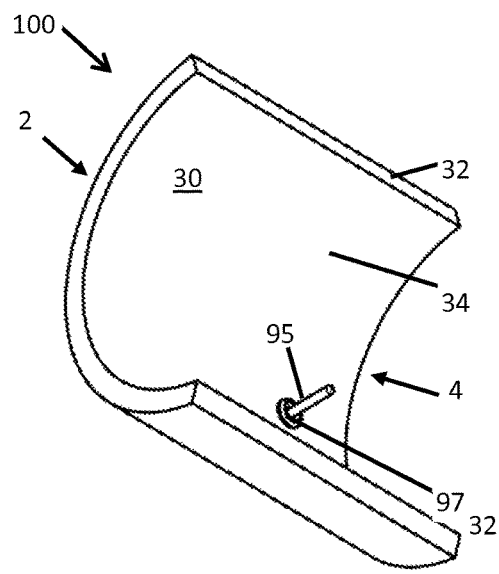
FIG. 13D is a perspective view of the concave surface of a single-arm collar embodiment having a stylet.

In a further embodiment, a portion of the lip 88 of the rigid extension seal 86 can extend beyond the side edges of the rigid collar. In other words the lip juts past the plane of the side edges such that they are not planar with each other. This can provide the advantage of the lip forming a more complete or more secure seal with the interior side of the pressure infusion cuff when they are pressed together. FIGS. 12B, 12C and 12D illustrate one example of a rigid extension seal where the lip extends past the side edges 32 of an arm of a rigid collar. With this embodiment, the lip forms a convex curve between the side edges, causing the blade edge to extend past the side edges, as shown in 12B.

In a particular embodiment, illustrated, for example, in FIGS. 11A-12D, the rigid extension seal extending from the proximal end 2 of an arm 30 is semi-spherical. In this embodiment, the rigid extension seal is a semi-spherical shape of between ¼ and ½ of a hemisphere, where the equatorial line 89 is at the point where the seal meets the proximal end 2 of the arm 30. In a more specific embodiment, the arc of curvature (AC) of the rigid extension seal is between ¼ and ⅝ of a hemisphere, such that the proximal end of the rigid extension seal 86 extends past the side edges of the arm. This can allow at least part of the lip 88 to contact a pressure infusion cuff before the side edges and provide sufficient pressure against a pressure infusion cuff to ensure that all or at least some portion, of the air pocket in an IV infusion bag is contained within the channel 70 and the contiguous void 87.

A specific embodiment of a rigid collar having a rigid extension seal can have an interior width (W), from one side edge to the other side edge, of between approximately 70 mm to approximately 75 mm. The height (H) of the rigid collar can be between approximately 45 mm and approximately 55 mm. The total height of this embodiment, which is the length from the distal end of the arm to the proximal end of the convex surface, can be between approximately 75 mm and 85 mm. In a further particular embodiment, the radius of curvature of the concave surface 34 of the arm 30 is approximately 41 mm and the radius of curvature of the lip 88 is approximately 115 mm. FIGS. 12A-12D illustrate an example of a rigid collar embodiment having dimensions within these ranges.

Another embodiment of a collar 9 of the subject invention is a flex collar 200 that can be used with almost any size fluid bag 5, can be used with any of a variety of types of pressure infusion cuffs 8, and can adjust the size of the channel 70 based on the amount of compression applied by the pressure infusion cuff. In one embodiment, a flex collar is a generally flat panel or sheet of a pre-determined thickness of semi-rigid material, as shown, for example, in FIG. 24A. Ideally, the material and/or dimensions, e.g., thickness, of the flex collar, allows all of most of the flex collar to bend or curve when sufficient force is applied, which can cause the side edges to bend or recurve, but resumes the generally flat configuration when force is not applied by the pressure infusion cuff. In other words, the material is biased to maintain a flat panel or sheet-like configuration, and can be bent, curved, or recurved to a shape similar to one or more of the rigid cuff embodiments, when force is applied. Thus, the material can have a pre-determined tensile strength that allows the flex collar to bend or curve up to a pre-determined distance. This can further inhibit the side edges 32 from coming together and pinching over or otherwise damaging the fluid bag or overlapping to the point that the side edges can damage the pressure infusion cuff or from the channel detrimentally constricting the bag. It is within the skill of a person trained in the art to determine which one or more of any of a variety of materials will provide the ideal tensile strength and the appropriate dimensions for a flex cuff utilizing the selected material. Such variations are within the scope of this invention.

Embodiments of a flex collar can be placed around or against any location on a fluid bag 6 and the flex collar and fluid bag placed within a pressure infusion cuff. How it gets placed in the pressure infusion cuff will depend upon the type of cuff used (flat opening or tubular). Initially, the flex collar can extend at least partially around the vertical edges 6 of the fluid bag, similarly to the embodiments of a rigid collar 100 that has wings 37. However, the flex collar can be more responsive to pressure and all or most of the flex collar can bend or curve in response to pressure from the pressure infusion cuff. In a particular embodiment, the flex collar can at least partially conform to the shape of the interior side 12 of a pressure infusion cuff as it expands. This can provide a channel 70 of an initial size to at least partially surround a fluid bag, as shown in the example in FIG. 24B. It can also ensure that one or more of the side edges are initially positioned or facing in the direction in which they can be brought closer together when the flex cuff is squeezed by a pressure infusion cuff. When the pressure infusion cuff inflates and expands around the flex collar and fluid bag, the flex collar will be constricted around the fluid bag, reducing the volume of the channel. However, as described above, the material of a flex collar is semi-rigid and has a pre-determined tensile strength. This can inhibit the flex collar from being bent or curved beyond a pre-determined point, ensuring that the channel is not compressed beyond a minimum diameter or volume. This can ensure that the channel retains a volume sufficient to contain, trap, or otherwise prevent air in the fluid bag from being forced out by the pressure infusion cuff.

As with the other embodiments described above, it is not required that a flex collar contain 100% of the air in a fluid bag. As long as the dimensions of a flex collar allow the channel to capture or contain at least 30%, 35%, 40%, 45%, 50%, 55%, 60%, 65%, 70%, 75%, 80%, 85%, 90%, 95%, and/or 99%, and/or an amount in a range between any two of the listed values, of the air within a fluid bag, it can be sufficient. Any uncaptured air can also be inhibited from entering the IV tubing, due to the decreased pressure on the bag by the presence of the collar. Fluid will continue to evacuate from the bag under gravitation force. Thus, it will be understood by the skilled artisan, that the width (W) and height (H) of a flex collar can vary considerably depending upon these and other factors. Such variations are within the scope of this invention.

In another embodiment, a flex collar can be incorporated into the structure of a pressure infusion collar. One non-limiting example shown in FIG. 24B has a flex collar at least partially attached to the interior surface 12 of a pressure infusion cuff. The side edges 32 extend sufficiently over the vertical sides 6 that when the pressure infusion cuff is placed around a fluid bag, the side edges of the flex cuff at least partially extend around the fluid bag. With this embodiment, the side edges of the flex cuff being unattached, allows them to recurve, bend, come closer together, or overlap as the pressure infusion cuff expands, constricting the flex collar and the channel.

The collar 9 embodiments of the subject invention, including clip collar 10, rigid collar, and flex collar embodiments, can be placed in any suitable location on an IV fluid bag 5. They can also be used with any of a variety of pressure infusion cuffs known in the art, including those that fold open and those that are more tubular or sleeve-like.

An alternative embodiment is configured for use around the bottom or proximal end 2 of an IV fluid bag. This embodiment, referred to as a shelf collar 350, can be similar to a rigid collar 100 embodiment having wings 37, as described above. This embodiment could be used around the distal end 4 of an IV fluid bag. However, it will be seen from the following description that it can be most effective when used at the proximal end 2 of a fluid bag.

Figure 25A:
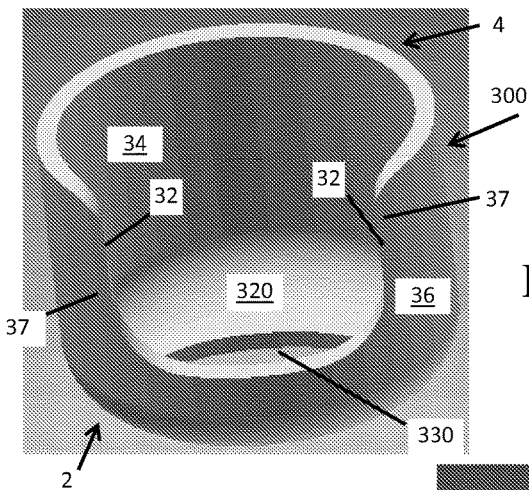
Figure 25B:
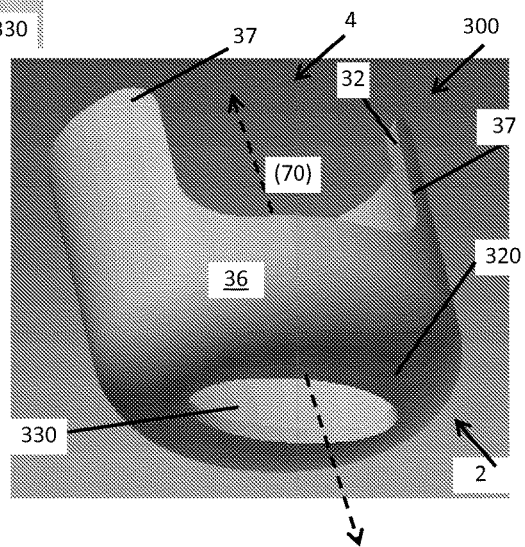
Figure 25C:
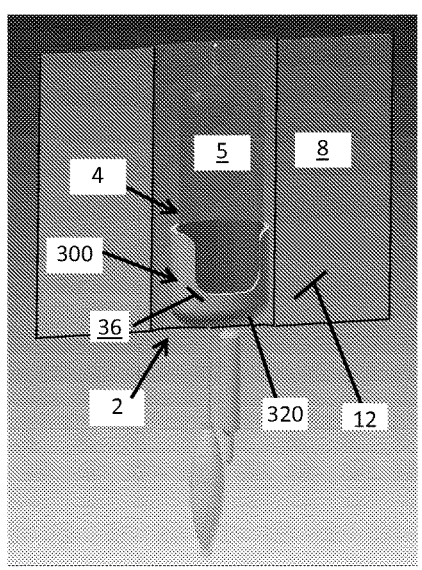

With this embodiment, a rigid collar 100 with wings 37 is modified with a shelf 320 fixedly attached across at least part of the proximal end 2, an example of which is shown in FIGS. 25A and 25B. The proximal end 2 of an IV fluid bag can be passed through the distal end 4 of the channel 70 of the shelf collar, so that the proximal end 2 rests or abuts against the shelf and the fluid bag is protected by one or more of the concave surface 34. In a further embodiment, the shelf 320 has a port 330 therethrough, contiguous with the channel 70, for the passage of tubes, wires, other lines, and other connections from the fluid bag through the shelf, so as to extend out from the proximal end, as shown in the example in FIG. 25C. When utilized with a pressure infusion cuff, the shelf collar 350 can be temporarily held against the proximal end of the fluid bag until such time that the pressure infusion cuff, inflated or otherwise, presses against the convex surfaces 36 of the shelf collar sufficiently to hold it in place against the fluid bag. One example of this is shown in FIG. 25C, where the shelf collar is emplaced while the pressure infusion cuff is open. When the pressure infusion cuff is closed, it can press against the convex surfaces of the collar.

In an alternative method, the fluid bag and pressure infusion cuff can be assembled and hung up for use. Tubing or other devices that extend from the proximal end of the fluid bag can be passed through the port 330 prior to being attached. Before the pressure infusion cuff is inflated, a shelf collar can be inserted through the proximal end 2 of the infusion cuff to go around the proximal end of the fluid bag therein. Tubes and other items attached to the fluid bag can extend down through the port. As the pressure infusion cuff inflates it can hold the shelf collar by frictional force around the proximal end of the fluid bag. The shelf collar can operate similarly to the rigid collar in that it inhibits the pressure infusion cuff from completely squeezing the fluid bag and provides an area in which any air within the bag will be trapped or captured, since it cannot be expelled into the tubing without application of direct force on the bag. Fluid can continue to drip out under the force of gravity, but air will be retained in the unsqueezed area within the channel.

Figure 11A:
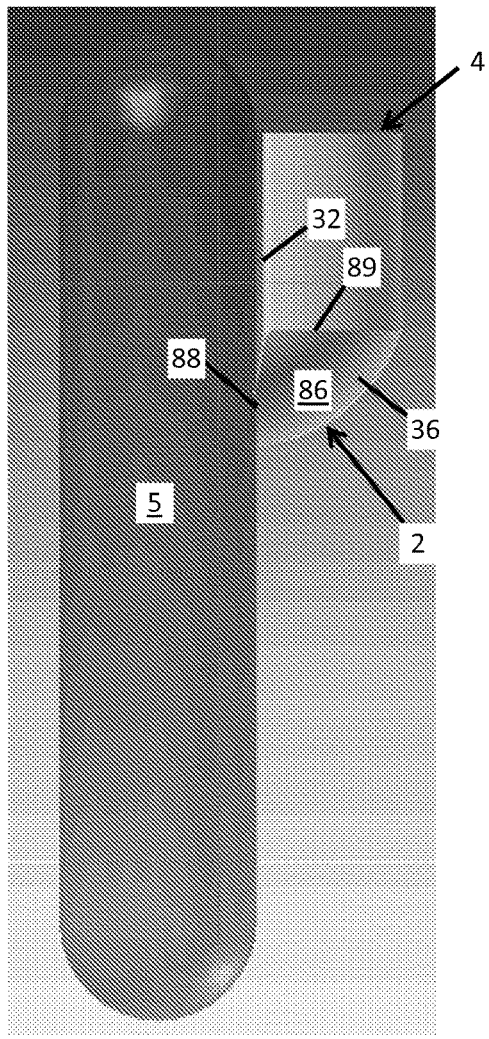
FIG. 11A is a side elevational view of a representative IV fluid bag showing a single-arm collar with a dome-like seal thereon.
Figure 11B:
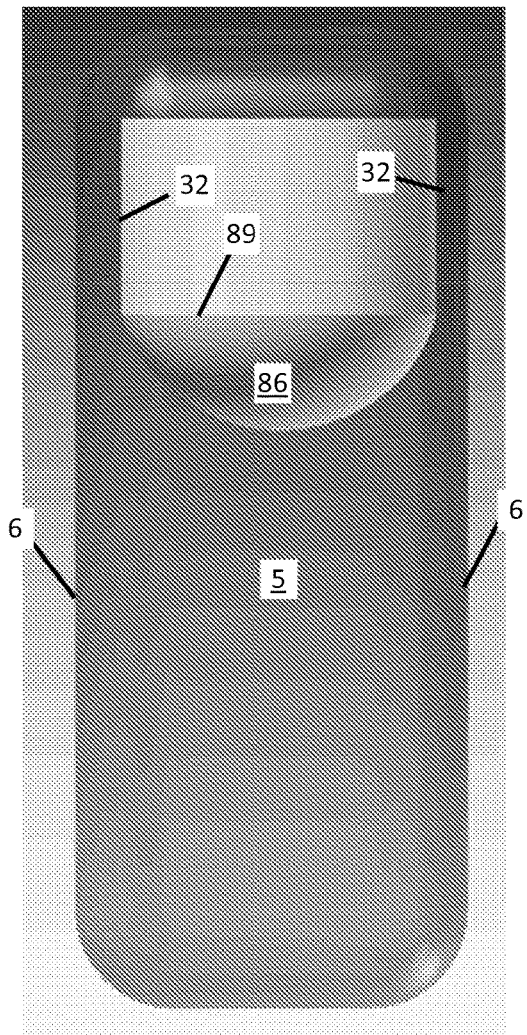
FIG. 11B is a front elevation view of a representative IV fluid bag showing a single-arm collar with a dome-like seal thereon.
Figure 11C:
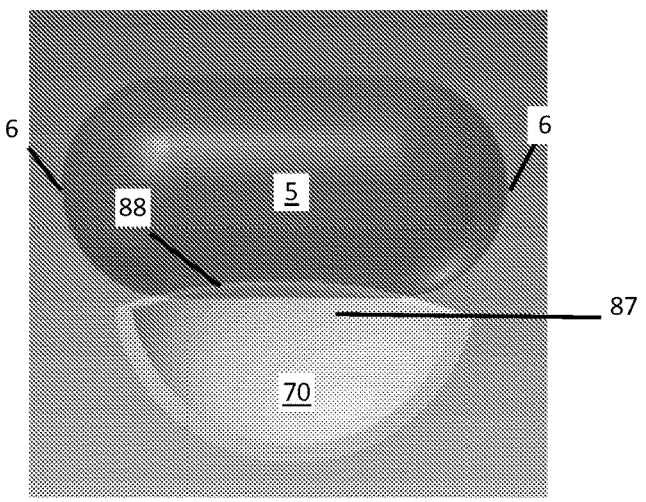
FIG. 11C is a distal end elevation view of a representative IV fluid bag showing a single-arm collar with a dome-like seal thereon.
Figure 11D:
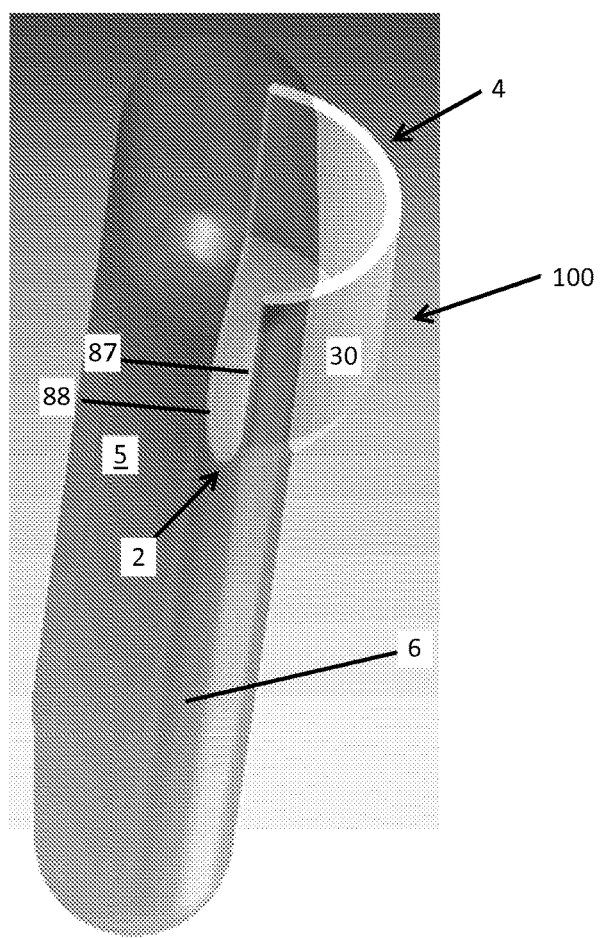
FIG. 11D is a distal end perspective view of a representative IV fluid bag showing a single-arm embodiment with a dome-like seal thereon.

A unique advantage of the embodiments of the subject invention is that they can be placed at any location, or at least more than one location, on an IV infusion bag. A filled IV infusion bag, viewed from a transverse plane, usually has a generally oval-shaped circumference, such that there is formed a front side and rear side of the bag, as illustrated, for example, in FIG. 7. The one or more arms of certain embodiments of the subject invention can be placed against the front and/or rear side of an infusion bag at any point on the bag. FIGS. 7 and 8A illustrate examples of a collar embodiment of the subject invention having two arms placed on either side of the bag and at or about the distal end 4 of a bag. Likewise, FIGS. 9A and 11A illustrate examples of a single-arm collar embodiment also placed at about the distal end of the bag. However, a collar can be placed closer to the proximal end or even at a middle-point on the bag. A person with skill in the art, having benefit of this disclosure, will be able to determine an appropriate position for a collar embodiment of the subject invention. The embodiments of the subject invention are therefore not limited to being placed in any one particular position or location on an IV infusion bag and any such variations in the placement are within the scope of this invention.

Figure 14:
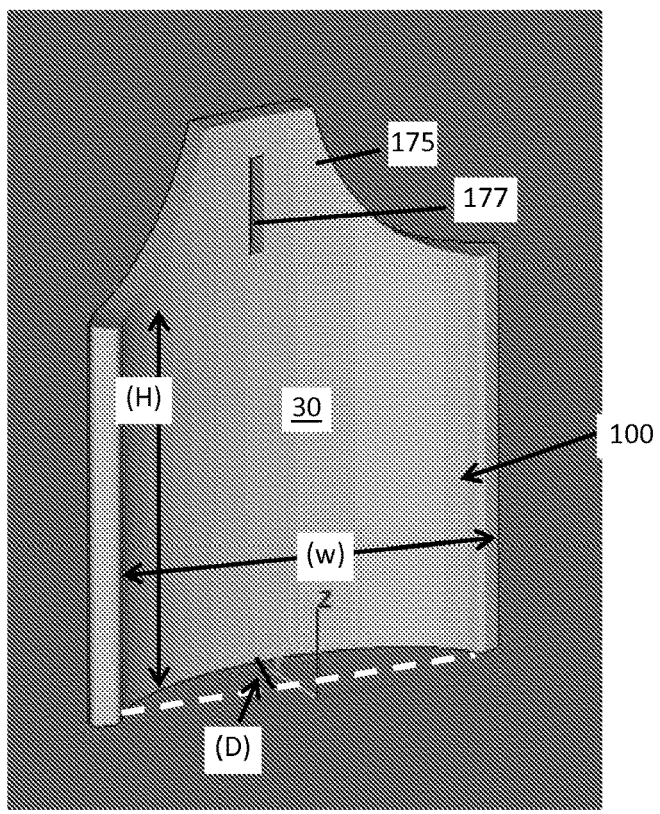
FIG. 14 is a perspective view of the concave surface of an embodiment having a hanging flange.
Figure 15:
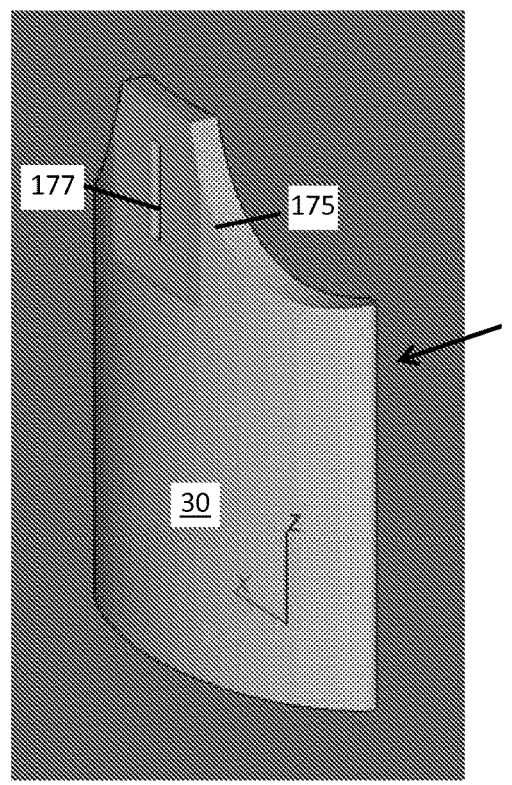
FIG. 15 is a perspective view of the convex surface of an embodiment having a hanging flange.

When a fluid infusion bag is emplaced within a pressure infusion cuff 8, the entire apparatus is usually hung from an IV pole. The interior surface of many pressure infusion cuffs includes a hanging mechanism or hook 300 on which the fluid infusion bag can be attached to prevent the fluid bag from slipping out of the pressure infusion cuff when it is hung from the IV pole. One example of a hook 300 utilized in a pressure infusion cuff is shown in FIGS. 14 and 15. A collar embodiment of the subject invention can also be secured in position around an IV fluid bag by utilizing this existing hook.

A collar can include a hanger 150 extending from the distal end 4 of an arm. A hanger can assume any of a variety of configurations that allow a collar embodiment of the subject invention to be secured to the hook 300 within a pressure infusion cuff. One advantageous position for a hanger would be at or near the center of the distal end of the arm. The hanger can be placed around a hook so that a collar is supported by or hangs from the hook and is prevented or inhibited from falling or sliding out of the pressure infusion cuff. The pressure infusion cuff, when wrapped around a collar and a fluid bag can ensure that the collar is held in the correct location on the fluid bag. In one embodiment, a hanger can be a flexible loop 150 of material fixedly attached to at or about the distal end of an arm 30. FIG. 3C illustrates one example of this type of flexible hanger 150.

Figure 16:
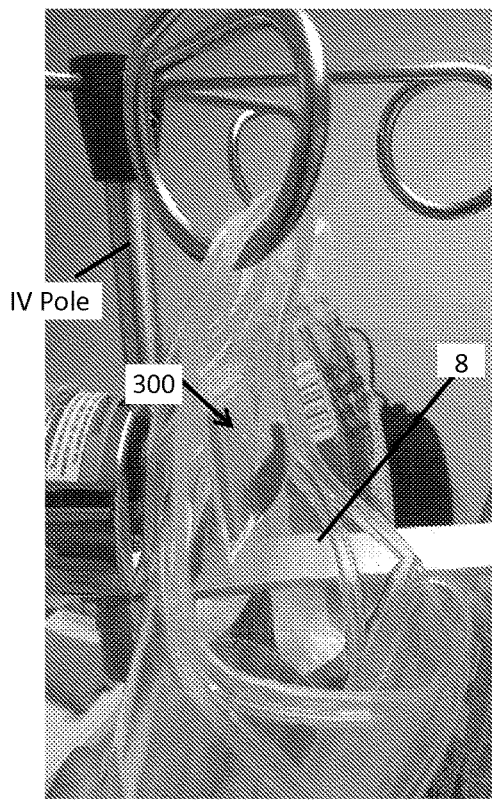
FIG. 16 is a photograph of a pressure infusion cuff showing a hanging hook.
Figure 17:
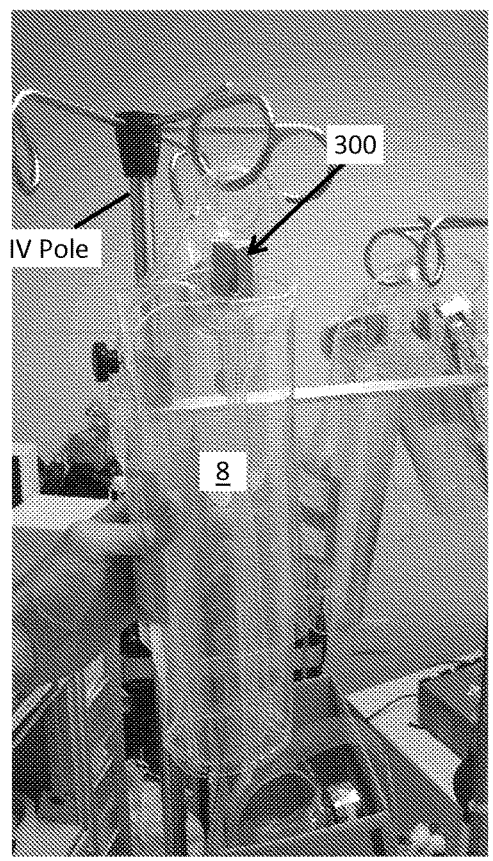
FIG. 17 is a photograph of a pressure infusion cuff showing an alternative view of a hanging hook.
Figure 18:
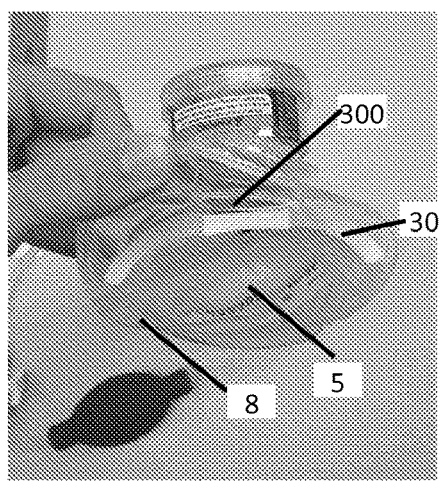
FIG. 18 is a photograph of a distal end view of a pressure infusion cuff with an infusion bag and an embodiment of a rigid collar having a hanger flange.
Figure 19:
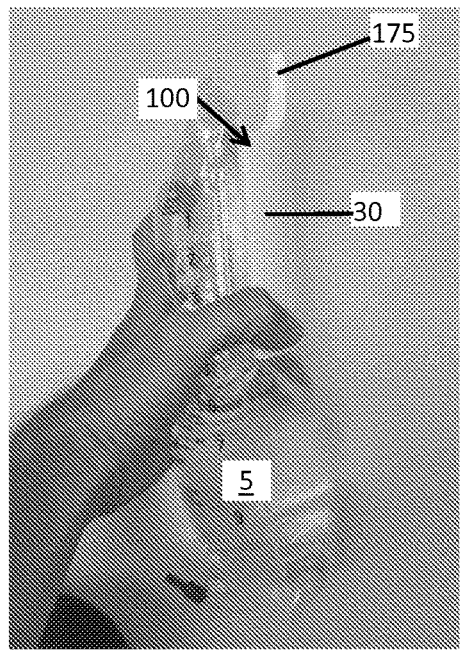
FIG. 19 is a photograph illustrating an embodiment of a rigid collar having a hanger flange and placed against an infusion bag.
Figure 20:
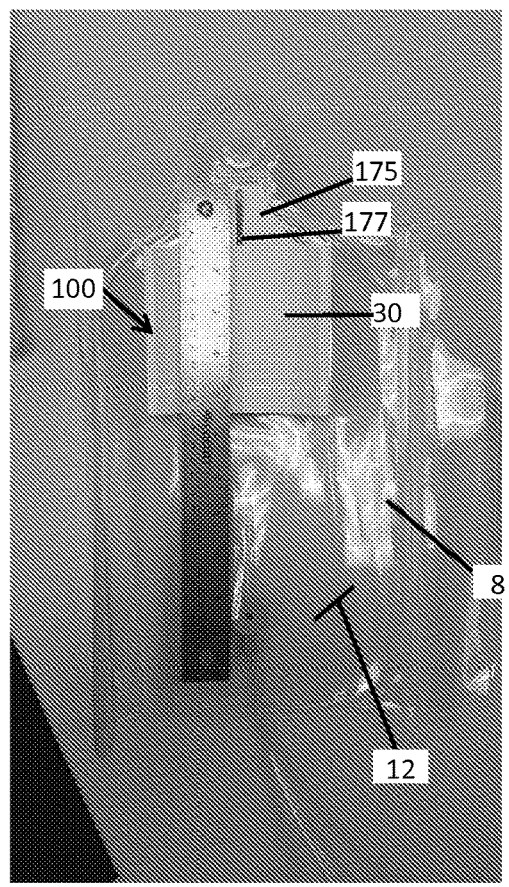
FIG. 20 is a photograph illustrating an embodiment of a rigid collar having a hanger flange attached to a hook in a pressure infusion cuff.

In another embodiment, a hanger is a rigid or semi-rigid flange 175 that extends from at or about the distal end 4 of an arm. A flange hanger can extend so as to be substantially collinear to the arm. Alternatively, it can extend at an angle to the arm, such that it bends or curves towards either the convex or the concave side of the arm. The flange can further have an opening therethrough that allows the flange to be placed on a hook 300. In one embodiment, the opening is in the form of a proximal-to-distal end slit 177 that can be placed over a hook. With this embodiment, when the slit is placed over the hook 300 in a pressure infusion cuff, the semi-rigid or rigid material of the flange helps to maintain the position of the collar around the fluid bag. FIGS. 16, 17, and 18 illustrate this embodiment, where the slit fits with minimal tolerance over the hook so that the flange can assist in holding the collar in position. Other hook configurations are also possible. Such variations that provide the same function, in substantially the same way, and provide substantially the same results are within the scope of this invention.

It should be understood from the above description that the collar embodiments of the subject invention can protect or inhibit a portion of an IV fluid bag from being completely compressed when used inside of a pressure infusion cuff. The collar 9 embodiments described herein can be utilized as a secondary component added to the combination of an IV fluid bag and a pressure infusion cuff. Alternatively, any of the collar embodiments could be incorporated with a pressure infusion cuff. There are any of a variety of mechanisms by which one or more of the collar embodiments of the subject invention can be permanently or removably attached to the interior surface 12 of a pressure infusion cuff, such that they are inseparable, at least during use.

Figure 24A:
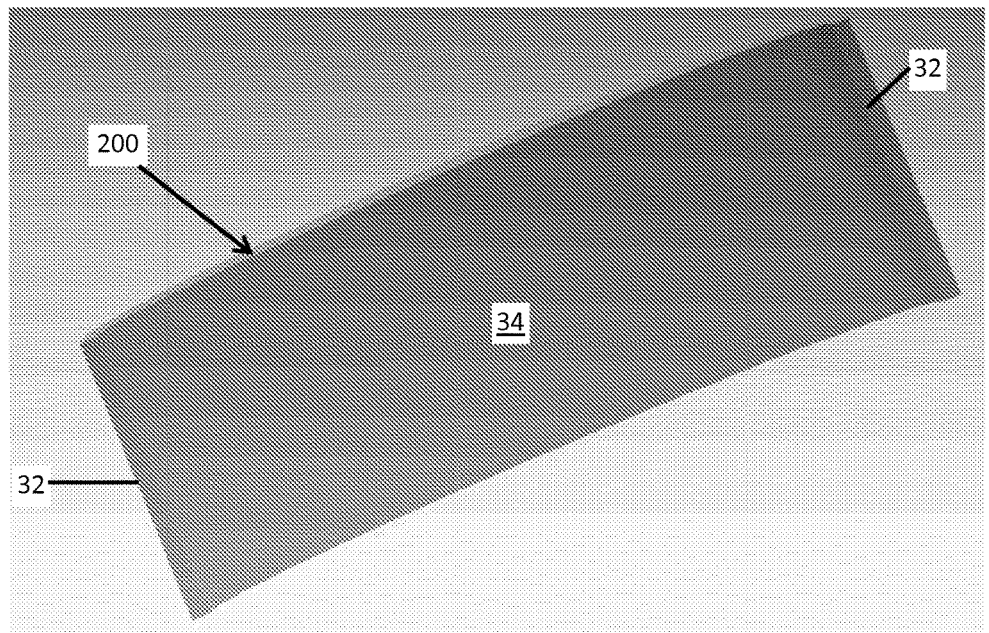
FIGS. 24A and 24B show an embodiment of a flex collar.
Figure 24B:
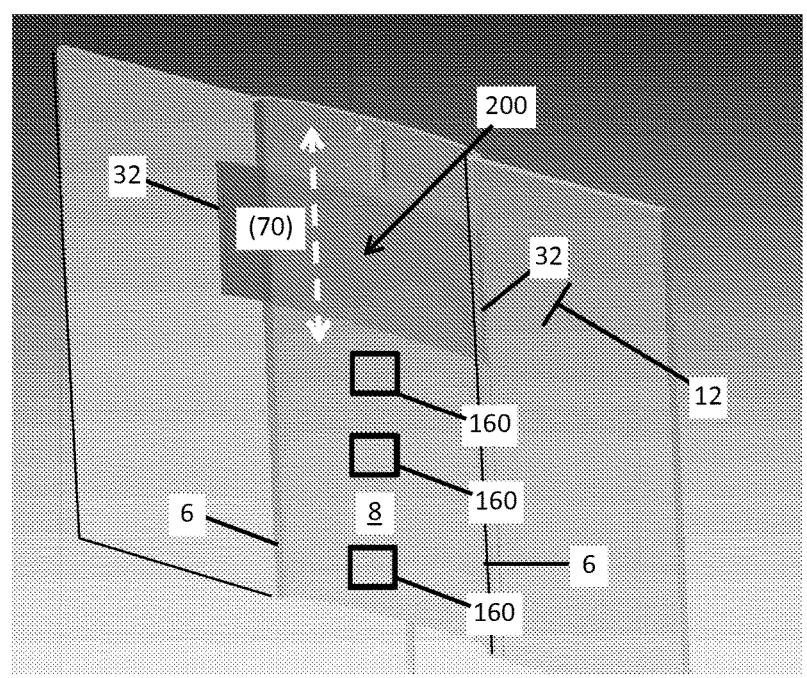

In one embodiment, the material of a collar can be fused or adhered or otherwise incorporated with the material of the interior surface 12 of an infusion cuff. By way of non-limiting example, all or some portion of a collar can be heat-fused to the interior surface 12 of a pressure infusion cuff. When a fluid bag is emplaced in the pressure infusion cuff, the incorporated collar can be simultaneously and advantageously positioned around the fluid bag. FIG. 24B illustrates a non-limiting example of a collar embodiment incorporated with the material of a pressure infusion cuff, such that it remains in place in the cuff, even when the cuff is open and/or uninflated.

In an alternative embodiment, a pressure infusion cuff and/or a collar can have coupling mechanisms 160 that allow a collar to be temporarily or removably attachable to the interior surface of a pressure infusion cuff. A non-limiting example of this would be hook and loop material utilized between the collar and the pressure infusion cuff, such that the collar can be removed and re-attached from the pressure infusion cuff as required. Alternative embodiments can employ snaps, hooks, flexible bands to go around the collar, buttons, and similar types of temporary attachment devices. A coupling mechanism can also be a pocket on the interior surface 12 of the pressure infusion cuff into which certain collar embodiments can be inserted. In a further embodiment, a pressure infusion cuff can have multiple coupling mechanisms, such that a collar can be placed at any advantageous position within the pressure infusion cuff.

FIG. 24B also illustrates an example of a pressure infusion cuff having multiple coupling mechanisms 160.

In an ideal situation, the air pocket in an IV infusion bag will actually be evacuated prior to the fluid bag being spiked or connected to the IV tubing for use. In emergency situations, there may not be time to conduct this extra step and the air pocket will remain in the fluid bag. Situations can arise where the presence of the air pocket is undesirable. For example, it may become apparent that the fluid bag will not be able to remain in a vertical position, which could place the air pocket in undesirable proximity to the IV tubing. In such situations, it would be helpful if the air pocket could be removed from the bag after it has been spiked.

FIGS. 13A-13D illustrate an embodiment having a stylet 95 on the concave surface 34 of a rigid collar 100. A stylet can be used to puncture a fluid bag above the level of the fluid in the bag, to release the air pocket. The stylet can further have a terminal end that is configured to puncture an IV bag only when sufficient force is applied between the fluid bag and the stylet. Force can be applied by a pressure infusion cuff or by a physician. In a further embodiment, a ring-seal 97 can be positioned around the base of the stylet, where it extends from the arm. The ring-seal can inhibit fluid from coming out of the puncture hole in the bag after the air pocket is released.

A stylet can be located anywhere on the concave surface. Ideally, the stylet can be positioned so that when it punctures a fluid bag, it initially hits the air pocket instead of the fluid. If a stylet is used it can be preferable for a collar to be placed closer to the distal end of a bag, but this is not required, as the bag can be punctured when the fluid level is lowered in the bag. FIGS. 13A-13D illustrate an embodiment where a stylet is centrally located on the concave surface and nearer to the distal end.

It should be understood from the above description that the collar embodiments of the subject invention are capable of protecting or inhibiting a portion of an IV fluid bag from being completely compressed when used with a pressure infusion cuff. The collar embodiments can be utilized as a secondary component added to the combination of an IV fluid bag and a pressure infusion cuff. Alternatively, any of the collar embodiments could be incorporated with a pressure infusion cuff. There are any of a variety of mechanisms by which one or more of the collar embodiments of the subject invention can be removably attached to the interior surface 12 of a pressure infusion cuff.

As mentioned above, the collar embodiments of the subject invention are useful for inhibiting a pressure infusion cuff from completely evacuating a fluid bag to the point where any air in the bag is forced into the fluid tubing. Thus, if there is an area of the fluid bag that is not compressed by the pressure infusion cuff, air in the fluid bag can normally be retained in or around that uncompressed area of the fluid bag. Modifications to a fluid bag and/or a pressure infusion cuff could also provide such uncompressed areas.

Usually, a fluid bag is generally flexible and is completely collapsible. In one embodiment, a fluid bag is modified to have a collar 9 incorporated as part of the structure of the fluid bag. A collar can be any of the above-described embodiments incorporated as part of the structure of a fluid bag. Alternatively, some portion of a fluid bag can be adapted to have a rigid area or portion of the material that is not flexible or collapsible. Such an area can be on one or both sides of a fluid bag. It could also be at either end of a fluid bag. FIGS. 26A-26E illustrate a non-limiting example of a collared fluid bag 500 having a rigid or semi-rigid cap collar 400 incorporated at the distal end 4 of the fluid bag, which can make some portion of the distal end incompressible or at least partially incompressible. For example, a cap collar could encompass or cover approximately the distal ⅕ to approximately the distal ⅓ of a fluid bag. As with the other embodiments described above, it is not required that the cap collar on a collared fluid bag contain 100% of the air in the fluid bag. As long as the dimensions of a cap collar allow the channel to capture or contain at least 30%, 35%, 40%, 45%, 50%, 55%, 60%, 65%, 70%, 75%, 80%, 85%, 90%, 95%, and/or 99%, and/or an amount in a range between any two of the listed values, of the air within a fluid bag, it can be sufficient. When utilizing a cap collar, gravity will allow fluid to continue to evacuate from the proximal end of the fluid bag. However, air or any other gas within the fluid bag will tend to stay above the fluid level in the bag. As the fluid level drops, the air or gas will remain in the uncompressed area above the fluid level. When a modified fluid bag is utilized with a pressure infusion cuff, the area with the incorporated collar, such as an incorporated cap collar, is inhibited from being compressed, thus also inhibiting the forced evacuation of any air in the fluid bag.

In one embodiment, such as shown for example in FIGS. 26A-26E, a collared fluid bag 500 can include a cap collar 400 incorporated at about the distal end 4 of a fluid bag. In an alternative embodiment, not shown, a cap collar can only partially surround, cover, or encompass, the distal end. A cap collar can be incorporated on one or both sides of the distal end. The factors that can be considered by those skilled in the art with regard to the choice of how a collar, such as a cap collar, of the subject invention can be incorporated with a fluid bag have been discussed above with regard to the incorporation of a collar with a pressure infusion cuff. Those factors are reasserted here with regard to the incorporation of a collar into or as part of the structure of a fluid bag. In a particular embodiment, the collar is adhered to the fluid bag. In a specific embodiment, the collar is heat-fused to a fluid bag. However, it is within the skill of a person trained in the art to determine the most appropriate way to join, incorporate or otherwise combine a collar with a fluid bag. Such variations are within the scope of the subject invention.

It is also possible for a pressure infusion cuff to be modified so as to inhibit the forced evacuation of air or gas within a fluid bag. A pressure infusion cuff is usually designed to surround and squeeze an entire fluid bag, as shown for example in FIGS. 22B and 22C, where it can be seen that an entire fluid bag 5 can be surrounded by the pressure infusion cuff 8. With this embodiment, the entire pressure infusion cuff can be inflated or enlarged.

In one embodiment, a pressure infusion cuff is modified with one or more noninflatable areas 11 that do not inflate or enlarge on a pressure infusion cuff, creating areas on a pressure infusion cuff that can be inhibited from squeezing or pressing against a fluid bag therein. Such areas can be portions of the modified pressure infusion cuff 600 that are designed not to inflate by any of various techniques known to those with skill in the art. Alternatively, noninflatable areas can be cut-out or missing areas on a modified infusion cuff 600 where there is no material at all to press against a fluid bag. This can allow for the natural creation of a pocket in a fluid bag in which air within the fluid bag can be contained or trapped. Said otherwise, by not compressing the entire fluid bag, air or gas within the fluid bag can be contained within the uncompressed area.

Figure 27:
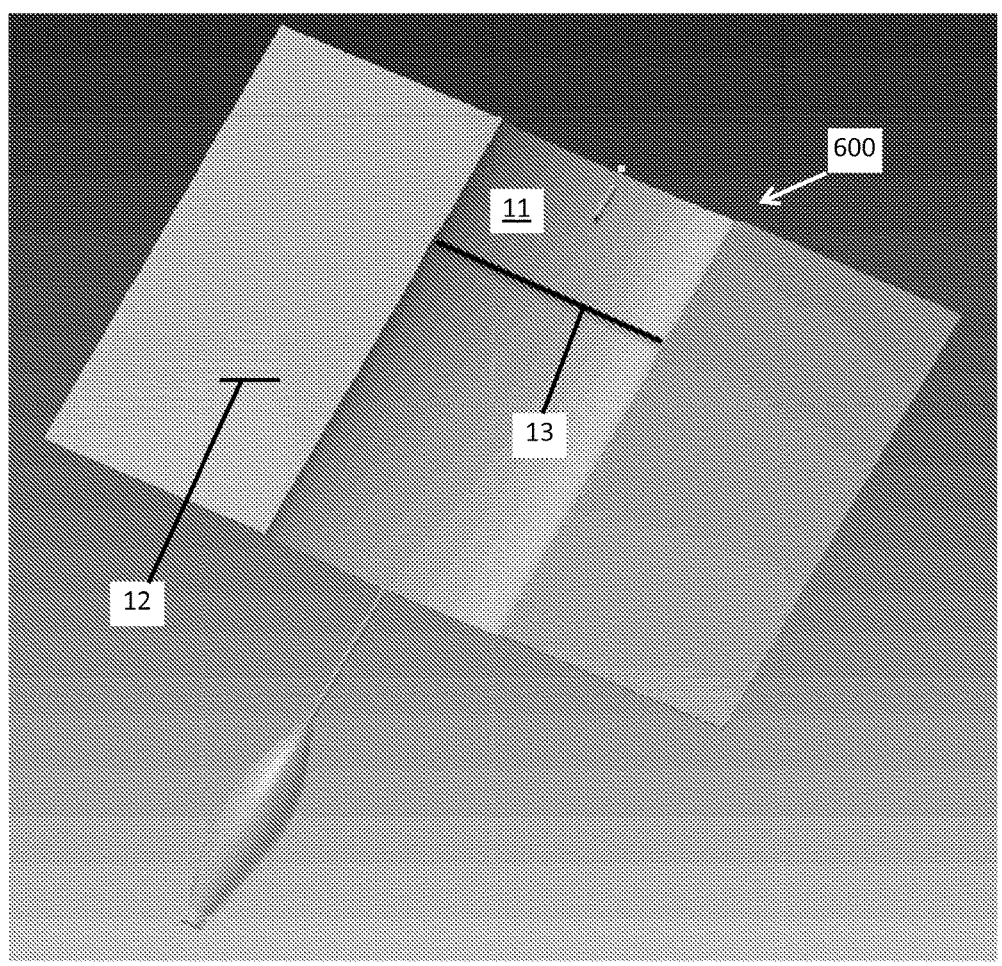
FIG. 27 is a perspective view of a modified pressure infusion cuff showing an area where the cuff does not inflate and thus does not press against a fluid bag therein.

FIG. 27 illustrates an example of a pressure infusion cuff having a noninflatable area. By way of non-limiting example, one or more sealing lines 13 can be formed across the pressure infusion cuff so as to fuse the cuff material and close off a portion of the cuff or otherwise inhibit the passage of air into the sealed-off area. A noninflatable area can also be an area specifically configured not to be inflatable. For example, it can be a single layer of material that can maintain structural integrity of the cuff, but which is not intended to contain air or apply pressure to a fluid bag.

In FIG. 27, the noninflatable area 11, here shown between the two vertical sides 6 of the fluid bag and above the sealing line 13, can be, by any of various techniques, prevented from inflating. However, in an alternative embodiment, the area between the sealing line and vertical sides can be absent or minimalized, such that this space or area of the cuff does not contact and/or squeeze the fluid bag. Furthermore, the noninflatable area can be on any location of the bag. FIG. 27 shows the noninflatable area at the back distal side of the pressure inflation cuff. However, it could just as easily be located on the front side and/or at the proximal end. The point being to place the noninflatable area where it will provide maximum benefit in inhibiting the forced evacuation of air from a fluid bag.

The embodiments of the subject invention provide a simple and easy to use device that addresses the problem of accidental embolisms due to air pockets in an IV fluid bag. The collar embodiments described herein can be easily incorporated with the use of a pressure infusion cuff on an IV fluid bag. By decreasing the amount of pressure applied to a fluid bag and/or creating a channel in which an air pocket can be contained, the chance of air in the fluid bag being forced into the IV tubing and into the patient are significantly reduced. The embodiments described herein can be used with any type of pressure infusion cuff. Alternatively, they can be incorporated into a pressure infusion cuff allowing them to be placed around a fluid bag simultaneously with the use of the pressure infusion cuff.

All patents, patent applications, provisional applications, and other publications referred to or cited herein are incorporated by reference in their entirety, including all figures and tables, to the extent they are not inconsistent with the explicit teachings of this specification. Additionally, the entire contents of the references cited within the references cited herein are also entirely incorporated by reference.

The examples and embodiments described herein are for illustrative purposes only and various modifications or changes in light thereof will be suggested to persons skilled in the art and are to be included within the spirit and purview of this application.

Any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. Further, when a particular feature, structure, or characteristic is described in connection with any embodiment, it is within the purview of one skilled in the art to affect such feature, structure, or characteristic in connection with other ones of the embodiments.

The invention has been described herein in considerable detail, in order to comply with the Patent Statutes and to provide those skilled in the art with information needed to apply the novel principles, and to construct and use such specialized components as are required. However, the invention can be carried out by specifically different equipment and devices, and various modifications, both as to equipment details and operating procedures can be effected without departing from the scope of the invention itself. Further, although the present invention has been described with reference to specific details of certain embodiments thereof and by examples disclosed herein, it is not intended that such details should be regarded as limitations upon the scope of the invention except as and to the extent that they are included in the accompanying claims.

I claim:

1. A method for inhibiting the evacuation of air from an intravenous fluid bag under compression by a pressure infusion cuff, the method comprising:

installing on an intravenous fluid bag a collar comprising, at least one arm having a proximal end, a distal end, at least one side edge, a convex surface against which the pressure infusion cuff can apply pressure, and a concave surface that forms a channel having a volume for containing at least a portion of the intravenous fluid bag, such that the volume formed by the concave surface of the at least one arm of the collar inhibits the pressure infusion cuff further inhibiting air within the intravenous fluid bag from being forcibly evacuated, securing the intravenous fluid bag, with the collar thereon inside the pressure infusion cuff.

2. The method, according to claim 1, further comprising: inflating the pressure infusion cuff so that at least a portion of an interior surface of the pressure infusion cuff exerts force against the convex surface of the at least one arm, thereby inhibiting the pressure infusion cuff from exerting force against the intravenous fluid bag within the volume of the concave surface.

3. The method, according to claim 2, wherein the volume of the channel is between approximately 125 cc and approximately 175 cc.

4. The method, according to claim 1, wherein the collar comprises at least two arms, where one side edge of each arm is adapted to be an articulating side and at least one other side edge of each arm is adapted to form a closing edge, such that when pressure is applied to the convex surfaces of the at least two arms, the articulating sides cause the side edges to come together and form at least one closing edge as fluid is evacuated from the intravenous fluid bag.

5. The method, according to claim 2, wherein the collar further comprises a coupling mechanism and the method further comprises attaching the collar to a pressure infusion cuff with the coupling mechanism.

6. The method, according to claim 5, wherein the collar further comprises a hanger operably attached to the at least one arm and the method comprises hanging the intravenous fluid bag on an IV pole prior to inflating the pressure infusion cuff.

7. A kit comprising:

an intravenous fluid bag;

tubing adapted to operably attach the intravenous fluid bag to a patient; and a collar, according to claim 1, to be placed against the intravenous fluid bag.

8. A kit, according to claim 7, further comprising a pressure infusion cuff, such that, when the collar is against the intravenous fluid bag and compressed by the pressure infusion cuff disposed around the collar and the intravenous fluid bag, the volume formed by the concave surface inhibits the portion of the intravenous fluid bag within the volume from being compressed and air within the intravenous fluid bag from being forcibly evacuated by the pressure infusion cuff.

\* \* \* \* \*